(12) United States Patent
Moran et al.

(10) Patent No.: US 8,792,973 B2
(45) Date of Patent: Jul. 29, 2014

(54) BIPOLAR SIEVE ELECTRODE AND METHOD OF ASSEMBLY

(75) Inventors: Daniel Moran, St. Louis, MO (US); Blaine Christiansen, St. Louis, MO (US); Matthew MacEwan, St. Louis, MO (US)

(73) Assignee: Washington University, St. Louis, MO (US)

( * ) Notice: Subject to any disclaimer, the term of this patent is extended or adjusted under 35 U.S.C. 154(b) by 190 days.

(21) Appl. No.: 13/130,262

(22) PCT Filed: Nov. 23, 2009

(86) PCT No.: PCT/US2009/065462
§ 371 (c)(1),
(2), (4) Date: Jun. 14, 2011

(87) PCT Pub. No.: WO2010/060011
PCT Pub. Date: May 27, 2010

(65) Prior Publication Data
US 2011/0251473 A1 Oct. 13, 2011

Related U.S. Application Data

(60) Provisional application No. 61/116,995, filed on Nov. 21, 2008.

(51) Int. Cl.
*A61B 5/04* (2006.01)
*A61N 1/00* (2006.01)

(52) U.S. Cl.
USPC ............ 600/544; 600/378; 600/545; 607/116

(58) Field of Classification Search
USPC ........................ 600/377–378, 393, 544–545; 607/115–116, 118
See application file for complete search history.

(56) References Cited

U.S. PATENT DOCUMENTS

| 5,400,784 A | 3/1995 | Durand et al. |
| 5,487,756 A * | 1/1996 | Kallesoe et al. ............... 607/118 |
| 5,897,583 A * | 4/1999 | Meyer et al. ................... 607/116 |
| 5,919,220 A * | 7/1999 | Stieglitz et al. ................ 607/118 |

(Continued)

FOREIGN PATENT DOCUMENTS

WO WO2010060011 A2 5/2010

OTHER PUBLICATIONS

Gregory T. A. Kovacs, Christopher W. Storment and Joseph M. Rosen, Regeneration Microelectrode Array for Peripheral Nerve Recording and Stimulation, IEEE Transactions on Biomedical Engineering, vol. 39, No. 9, Sep. 1992, pp. 893-902.

(Continued)

*Primary Examiner* — Linda Dvorak
*Assistant Examiner* — Brian M Antiskay
(74) *Attorney, Agent, or Firm* — Armstrong Teasdale LLP

(57) ABSTRACT

Apparatus for providing an interface between a nerve and an external information system. The apparatus includes a substrate having a first surface, an opposite second surface, and an electrode body, wherein the electrode body includes a plurality of holes extending therethrough. The apparatus also includes a plurality of electrical leads embedded within the substrate and a plurality of ring electrodes, wherein each of the ring electrodes circumscribes a corresponding hole, and wherein at least a portion of the ring electrodes is positioned on each of the first surface and the second surface.

16 Claims, 10 Drawing Sheets

(56) References Cited

U.S. PATENT DOCUMENTS

| | | | |
|---|---|---|---|
| 2002/0122770 A1 | 9/2002 | Oka et al. | |
| 2004/0111140 A1 | 6/2004 | Stieglitz et al. | |
| 2008/0033502 A1* | 2/2008 | Harris et al. | 607/45 |
| 2008/0228240 A1* | 9/2008 | Edell et al. | 607/48 |

OTHER PUBLICATIONS

Matthew D. Wood and Shelly E. Sakiyama-Elbert, Release Rate Controls Biological Activity of Nerve Growth Factor Released from Fibrin Matrices Containing Affinity-Based Delivery Systems, Wiley InterScience, 2007, pp. 300-312, Wiley Periodicals, Inc.

Gurpreet S. Dhillon, MD, et al., Residual Function in Peripheral Nerve Stumps of Amputees: Implications for Neural Control of Artificial Limbs, The Journal of Hand Surgery, pp. 605-615, 2004 by the American Society for Surgery of the Hand.

Claude Veraart, Warren M. Grill and J. Thomas Mortimer, Selective Control of Muscle Activation with a Multipolar Nerve Cuff Electrode, IEEE Transactions on Biomedical Engineering, vol. 40, No. 7, Jul. 1993, pp. 640-653.

Daniel McDonnall, Gregory A. Clark and Ricahrd A. Normann, Selective Motor Unit Recruitment via Intrafascicular Multielectrode Stimulation, Can. J. Physiol. Pharmacol 82, (2004), pp. 599-609.

Almut Branner, Richard B. Stein and Richard A. Normann, Selective Stimulation of Cat Sciatic Nerve Using an Array of Varying-Length Microelectrodes, Journal of Neurophysiology 85, 2001, pp. 1585-1594, The American Physiological Society.

Jamille F. Hetke, et al., Silicon Ribbon Cables for Chronically Implantable Microelectrode Arrays, IEEE Transactions on Biomedical Engineering, vol. 41, No. 4, Apr. 1994, pp. 314-321.

Gregory T. A. Kovacs, et al., Silicon-Substrate Microelectrode Arrays for Parallel Recording of Neural Activity in Peripheral and Cranial Nerves, IEEE Transactions of Biomedical Engineering, vol. 41, No. 6, Jun. 1994, pp. 567-577.

Jit Muthuswamy, Murat Okandan and Nathan Jackson, Single Neuronal Recordings Using Surface Micromachined Polysilicon Microelectrodes, Journal of Neuroscience Methods 142 (2005), pp. 45-54, Elsevier.

Craig T. Nordhausen, Edwing M. Maynard and Richard A. Normann, Single Unit Recording Capabilities of a 100 Microelectrode Array, Brain Research 726 (1996), pp. 129-140, Elsevier.

Qing Bai and Kensall D. Wise, Single-Unit Neural Recording with Active Microelectrode Arrays, IEEE Transactions on Biomedical Engineering, vol. 48, No. 8, Aug. 2001, pp. 911-920.

Rajarshi Saha and Jit Muthuswamy, Structure-Property Relationships in the Optimization of Polysilicon Thin Films for Electrical Recording/Stimulation of Single Neurons, Biomed Microdevices (2007) 9, pp. 345-360, Springer.

Daniel K. Leventhal and Dominique M. Durand, Subfascicle Stimulation Selectivity with the Flat Interface Nerve Electrode, Annals of Biomedical Engineering, vol. 31, 2003, pp. 643-652.

Richard A. Normann, Technology Insight: Future Neuroprosthetic Therapies for Disorders of the Nervous System, Nature Clinical Practice Neurology, vol. 3, No. 8, Aug. 2007, pp. 444-452.

Richard H. Gelberman, MD., et al., The Early Effects of Sustained Platelet-Derived Growth Factor Administration on the Functional and Structural Properties of Repaired Intrasynovial Flexor Tendons: An In vivo Biomechanic Study at 3 Weeks in Canines, The Journal of Hand Surger, pp. 373-379.

Stephanie M. Wilerth, et al., The Effects of Soluble Growth Factors on Embryonic Stem Cell Differentiation Inside of Fibrin Scaffolds, Stem Cells, 2007; 25, pp. 2235-2244, Embryonic Stem Cells.

Lars Wallman, et al., The Geometric Design of Micromachined Silicon Sieve Electrodes Influences Functional Nerve Regeneration, Biomaterials 22 (2001), pp. 1187-1193, Elsevier.

Chungkeun Lee, et al., The Measurement of compound Neural Action Potential in Sciatic Nerve Using Microelectrode Array, Proceedings of the 28th IEEE EMBS Annual International Conference New York City, USA, Aug. 30-Sep. 3, 2006, pp. 3002-3004.

Sophie Mailey, et al., Thin Film Platinum cuff Electrodes for Neurostimulation: In Vitro Approach of Safe Neurostimulation Parameters, Bioelectrochemistry 63 (2004), Science Direct, pp. 359-364, Elsevier.

Burkhard Schlosshauer, et al., Towards Micro Electrode Implants: In Vitro Guidance of Rat Spinal Cord Neurites through Polyimide Sieves by Schwann Cells, Brain Research 903 (2001), pp. 237-241, Elsevier.

Kevin J. Otto, Matthew D. Johnson and Daryl R. Kipke, Voltage Pulses Change Neural Interface Properties and Improve Unit Recordings with Chronically Implanted Microelectrodes, IEEE Transactions on Biomedical Engineering, vol. 53, No. 2, Feb. 2006, pp. 333-340.

Nitish Kumar, Brain Computer Interface, Cochin University of Science & Technology, Kochi-682022, Aug. 2008, pp. 1-52.

Jess Bartels, Dinal Andreasen, Princewill Ehirim, Hui Mao, Steven Seibert, E. Joe Wright, and Philip Kennedy, Neurotrophic Electrode: Method of Assembly and Implantation into Human Motor Speech Cortex, J. Neurosci Methods, Sep. 30, 2008; 174(2): 168-176.

Electrocorticography, Source: http://en.wikipedia.org/w/index.php?oldid=454966805, pp. 1-6.

B. Christiansen, Design of a 64-channel sieve electrode for stimulation of peripheral nerves, 13 pages.

O. Billoint, et al., A 64-Channel ASIC for In-Vitro Simultaneous Recording and Stimulation of Neurons Using Microelectrode Array, Aug. 23-26, 2007, pp. 6069-6072, Proceedings of the 29th Annual International Conference of the IEEE EMBS, Cite Internationale, Lyon France.

T. Stieglitz, et al., A Biohybrid System to Interface Peripheral Nerves After Traumatic Lesions: Design of a High Channel Sieve Electrode, Biosensors and Bioelectronics 17 (2002), pp. 685-696, Department of Sensor System/ Microsystems, Fraunhofer Institute for Biomedical Engineering, Ensheimer Strasse 48, D-66386 St. Ingbert, Germany.

S. Hafizovic, et al., A CMOS-Based Microelectrode Array for Interaction with Neuronal Cultures, Journal of Neuroscience Methods 164 (2007), pp. 93-106, Physical Electronic Laboratory, ETH Zurich, Wolfgang-Pauli Str. 16, 8093 Zurich, Switzerland, Department of Physics, University of Kaiserslautern, Kaiserslautern, Germany.

T. Stieglitz, et al., A Flexible, Light-Weight Multichannel Sieve Electrode With Integrated Cables for Interfacing Regenerating Peripheral Nerves, Sensors and Actuators A 60 (1997), pp. 240-243, Fraunhofer Institute for Biomedical Engineering, Department of Sensor Systems/Microsystems, Ensheimer Strasse 48, D-66386 St. Ingbert, Germany.

Stephen A. Boppart, et al., A Flexible Perforated Microelectrode Array for Extended Neural Recordings, IEEE Transactions on Biomedical Engineering, vol. 39, No. 1, Jan. 1992, pp. 37-42.

Sam Musallam, et al. A Floating Metal Microelectrode Array for Chronic Implantation, Journal of Neuroscience Methods 160 (2007), pp. 122-127, California Institute of Technology, Division of Biology, MC 216-76 Pasadena, CA 91125, United States.

David H. Liang, et al., A Method for Evaluating the Selectivity of Electrodes Implanted for Nerve Simulation, IEEE Transaction on biomedical Engineering, vol. 38, No. 5, May 1991, pp. 443-449.

Tayfun Akin, et al., A Micromachined Silicon Sieve Electrode for Nerve Regeneration Applications, IEEE Transactions on Biomedical Engineering, vol. 41, No. 4, Apr. 1994, pp. 305-313.

Matthew A. Schiefer, et al., A Model of Selective Activation of the Femoral Nerve with a Flat Interface Nerve Electrode for a Lower Extremity Neuroprosthesis, IEEE Transactions on Neural Systems and Rehabilitation Engineering, vol. 16, No. 2, Apr. 2008, pp. 195-204.

Almut Branner and Richard Alan Normann, A Multielectrode Array for Intrafascicular Recording and Stimulation in Sciatic Nerve of Cats, Brain Research Bulletin, vol. 51, No. 4, pp. 293-306, Center for Neural Interfaces, Department of Bioengineering, University of Utah, Salt Lake City, UT, USA.

Richard A. Normann, et al., A Neural Interface for a Cortical Vision Prosthesis, Vision Research 39 (1999), pp. 2577-2587, Pergamon, Department of Bioengineering, University of Utah, Salt Lake City, UT USA.

(56) References Cited

OTHER PUBLICATIONS

T. Kawada, et al., A Sieve Electrode as a Potential Autonomic Neural Interface for Bionic Medicine, Proceedings of the 26th Annual International Conference of the IEEE EMBS, pp. 4318-4321, San Francisco, CA USA, Sep. 1-5, 2004.
Patrick K. Campbell, et al., A Silicon-Based, Three-Dimensional Neural Interface: Manufacturing Processes for an Intracortical Electrode Array, IEEE Transactions on Biomedical Engineering, vol. 38, No. 8, Aug. 1991.
Arunkumar N. Badi, MD., et al., A Technique for Implantation of a 3-Dimensional Penetrating Electrode Array in the Modiolar Nerve of Cats and Humans, pp. 1019-1025, Arch Otolaryngol Head Neck Surg/vol. 138, Sep. 2002, www.archoto.com at Washington University—St. Louis, MO USA.
International Search Report and Written Opinion of PCT/US2009/065462 Dated Jul. 8, 2010.
Arnold C. Hoogerwerf and Kensall D. Wise, A Three-Dimensional Microelectrode Array for Chronic Neural Recording, IEEE Transactions on Biomedical Engineering, vol. 41, No. 12, Dec. 1994, pp. 1136-1146.
Robert Rieger, et al., Very Low-Noise ENG Amplifier System Using CMOS Technology, IEEE Transactions on Neural Systems and Rehabilitation Engineering, vol. 14, No. 4, Dec. 2006, pp. 427-437.
Maysam Ghovanloo and Khalil Najafi, A Wireless Implantable Multichannel Microstimulating System-on-a-Chip With Modular Architecture, IEEE Transactions on Neural Systems and Rehabilitation Engineering, vol. 15 No. 3, Sep. 2007, pp. 449-457.
Malagodi MS, Horch KW, Schoenberg AA., An Intrafascicular Electrode for Recording of Action Potentials in Peripheral Nerves, Ann Biomed Eng. 1989—PUbMed, 1 page.
Yoshida K, and Stein RB, Characterization of Signals and Noise Rejection with bipolar Longitudinal Intrafascicular Electrodes, IEEE Trans Biomed Eng. Feb. 1999; 46(2):226-34, 1 page.
De Haro C., et al., Electrochemical Platinum Coatings for Improving Performance of Implantable Microelectrode Arrays, Biomaterials, Dec. 2002, 23 (23:4515-21, 1 page.
Walter JS, et al., Evaluation of a Thin-Film Peripheral Nerve Cuff Electrode, J. Spinal Cord Med. Jan. 1995; 18(1): 28-32, 1 page.
Robert M. Bradley, et al., Functional Regeneration of Glossopharyngeal Nerve through Micromachined Sieve Electrode Arrays, ScienceDirect—Brain Research, pp. 1-2.
Stieglitz T., et al., Initial Chronic Results of flexible Sieve Electrodes as Interface to Nerve Stumps [Article in German], Biomed tech (Berl), 2002;47 Suppl 1 Pt 2:692-5, 1 page.
Ceballos D. Valero-Cabre, et al. Morphologic and Functional Evaluation of Peripheral Nerve Fibers Regenerated Through Polyimide Sieve Electrodes Over Long-Term Implantation, J Biomed Mater Res, Jun. 15, 2002; 60(4): 517-28, 1 page.
Dario P. Garzella, et al., Neural Interfaces for Regenerated Nerve Stimulation and Recording, IEEE Trans Rehabil Eng. Dec. 1998; 6(4), 1 page.
Stieglitz T. Schuettler and M. Koch KP, Neural Prostheses in Clinical Applications—Trends From Precision Mechanics Towards Biomedical Microsystems in Neurological Rehabilitation, Biomed Tech (Berl), Apr. 2004;49 (4):72-7, 1 page.
Wallman L., et al., Perforated Silicon Nerve Chips with Doped Registration Electrodes: in Vitro Performance and In Vivo Operation, IEEE Trans Biomed Eng. Sep. 1999;46(9): 1065-73; 1 page.
Grill WM Jr. and Mortimer JT, Quantification of Recruitment Properties of Multiple Contact Cuff Electrodes, IEEE Trans Rehabil Eng Jun. 1996;4(2): 49-62, 1 page.
Navarro X, et al., Selective Fascicular Stimulation of the Rat Sciatic Nerve with Multipolar Polyimide Cuff Electrodes, Restor Neurol Neurosci, 2001; 18(1):9-21, 1 page.
Biyu J. He et al., Electrophysiological correlates of the brain's intrinsic large-scale functional architecutre, vol. 105, Oct. 14, 2008, pp. 16039-16044.
Biyu J. He et al., The fMRI Signal, Slow Cortical Potential and Consciousness, Mallinckrodt Institute of Radiology, Washington School of Medicine, St. Louis, MO, USA, Jun. 15, 2009, pp. 302-309.
Andrew S. S. Rice, et al., The Electrophysiological consequences of Electrode Impalement of Peripheral Nerves in the Rat, ScienceDirect—Brain Research, pp. 1-2.
Steve M. Laawrence, et al., Acute Peripheral Nerve Recording Characteristics of Polymer-Based Longitudinal Intrafascicular Electrodes, IEEE Transactions on Neural Systems and Rehabilitation Engineering, vol. 12, No. 3, Sep. 2004, pp. 345-348.
Spencer L. Smith, Jack W. Judy and Thomas S. Otis, An Ultra Small Array of Electrodes for Stimulating Multiple Inputs into a Single Neuron, Journal of Neuroscience Methods 133 (2004), pp. 109-114.
Jeffrey C. Petruska, Charles H. Hubscher and Richard D. Johnson, Anodally Focused Polarization of Peripheral Nerve Allows Discrimination of Myelinated and Unmyelinated Fiber Input to Brainstem Nuclei, Exp Brain Res (1998) 121, pp. 379-390, Springer-Verlag 1998.
Stephanie M. Willerth and Shelly E. Sakiyama-Elbert, Approaches to Neural tissue Engineering Using Scaffolds for Drug Delivery, ScienceDirect, Advanced Drug Delivery Reviews 59 (2007), pp. 325-338, Elsevier.
Natalia Lago, et al., Assessment of biocompatibility of Chronically Implanted Polyimide and Platinum Intrafascicular Electrodes, IEEE Transactions on Biomedical Engineering, vol. 54, No. 2, Feb. 2007, pp. 281-290.
Roy H. Olsson, III, et al., Band-Tunable and Multiplexed Integrated Circuits for Simultaneous Recording and Stimulation With Microelectrode Arrays, IEEE Transaction on Biomedical Engineering, vol. 52, No. 7, Jul. 2005, pp. 1303-1311.
Yoichiro Aoyagi, et al., Capabilities of a Penetrating Microelectrode Array for Recording Single Units in Dorsal Root Ganglia of the Cat, Journal of Neuroscience Methods 128 (2003), pp. 9-20, Elsevier.
A. Blau, et al, Characterization and Optimization of Microelectrode Arrays for in vivo Nerve Signal Recording and Stimulation, Biosensors & Bioelectronics vol. 12, No. 9-10, 1997, pp. 883-892, Elsevier Science Limited.
Daniel K. Leventhal, Mark Cohen, and Dominique M. Durand, Chronic Histological Effects of the Flat Interface Nerve Electrode, Journal of Neural Engineering Eng 3 (2006), pp. 102-113, Institute of Physics Publishing.
Daniel K. Leventhal and Dominique M. Durand, Chronic Measurement of the Stimulation Selectivity of the Flat Interface Nerve Electrode, IEEE Transactions of Biomedical engineering, vol. 51, No. 9, Sep. 2004, pp. 1649-1658.
Allen F. Mensinger, et al., Chronic Recording of Regenerating VIIIth Nerve Axons with a Sieve Electrode, J Neurophysiology 83: 2000, pp. 611-615.
Dustin J. Tyler and Dominique M. Durand, Chronic Response of the Rat Sciatic Nerve to the Flat Interface Nerve Electrode, Annals of Biomedical Engineering, vol. 31, 2003, pp. 633-642, Biomedical engineering Society.
Blake Murphy, Charles Krieger and Joaquin-Andres Hoffer, Chronically Implanted Epineural Electrodes for Repeated Assessment of Nerve Conduction Velocity and Compound Action Potential Amplitude in Rodents, Journal of Neuroscience Methods 132 (2004), pp. 25-33, Elsevier.
J.S. Lin, et al., CMOS-Micromachined, Two-Dimenisional Transistor Arrays for Neural Recording and Stimulation, Proceedings of the 29th Annual International Conference of the IEEE EMBS, Aug. 23-26, 2007, pp. 2365-2368.
Todd Hillman, et al., Cochlear Nerve Stimulation with a 3-Dimensional Penetrating Electrode Array, Otology & Neurotology 24, 2003, pp. 764-768, Departments of Otolaryngology and Bioengineering, University of Salt Lake City, Utah, USA.
Shelly E. Sakiyama-Elbert and Jeffrey A. Hubbell, Controlled Release of Nerve Growth Factor From a Heparin-Containing Fibrin-Based Cell Ingrowth Matrix, Journal of Controlled Release 69 (2000), pp. 149-158, Elsevier.
Annie C. Lee, et al., Controlled Release of Nerve Growth Factor Enhances Sciatic Nerve Regeneration, Experimental Neurology 184 (2003), pp. 295-303, Science Direct, Academic Press.
Sara J. Taylor, John W. McDonald III and Shelly E. Sakiyama-Elbert, Controlled Release of Neurotrophin-3 from Fibrin Gels for Spinal Cord Injury, Journal of Controlled Release, 98 (2004), pp. 281-294, Science Direct, Elsevier.

(56) References Cited

OTHER PUBLICATIONS

Wood, MD, Borschel, GH, and Sakiyama-Elbert SE, Controlled Release of Glial-Derived Neurotrophic Factor Form Fibrin Matrices Containing an Affinity-Based Delivery System, J Biomed Mater Res A, May 8, 2008, 1 page.
Sara J. Taylor, et al., Delivery of Neurotrophin-3 from Fibrin Enhances Neuronal Fiber Sprouting after Spinal Cord Injury, Journal of Controlled Release 113 (2006), pp. 226-235, Science Direct, Elsevier.
Erin Patrick, et al., Design and Fabrication of a Flexible Substrate Microelectrode Array for Brain Machine Interfaces, Proceedings of the 28th IEEE EMBS Annual International Conference, New York City, USA, Aug. 30-Sep. 2006, pp. 2966-2969.
Anup Ramachandran, et al., Design, in vitro and in vivo Assessment of a Multi-Channel Sieve Electrode with Integrated Multiplexer, Journal of Neural Engineering, 3 (2006) pp. 114-124, Institute of Physics Publishing.
Shelly E. Sakiyama-Elbert and Jeffrey A. Hubbell, Development of Fibrin Derivatives for Controlled Release of Heparin-Binding Growth Factors, Journal of Controlled Release 65 (2000), pp. 389-402, Elsevier.
Shelly E. Sakiyama-Elbert, Alyssa Panitch and Jeffrey A. Hubbell, Development of Growth Factor Fusion Proteins for Cell-Triggered Drug Deliver, The FASEB Journal express article 10.1097/00-0564je, Mar. 20, 2001, 17 pages.
Dustin J. Maxwell, et al., Development of Rationally Designed Affinity-Based Drug Delivery Systems, Acta Biomaterialia 1 (2005), pp. 101-113, Science Direct, Elsevier.
P. Negredo, et al., Differential Growth of Axons From Sensory and Motor Neurons Through a Regenerative Electrode: A Stereological, Retrograde Tracer, and Functional Study in the Rat, Neuroscience 128 (2004), pp. 605-615, Elsevier.
Sara J. Taylor and Shelly E. Sakiyama-Elbert, Effect of Controlled Delivery of Neurotrophin-3 From Fibrin on Spinal Cord Injury in a Long Term Model, Journal of Controlled Release, 116 (2006), pp. 204-210, Science Direct, Elsevier.
Zeng Lertmanorat, Kenneth J. Gustafson and Dominique M. Durand, Electrode Array for Reversing the Recruitment Order of Peripheral Nerve Stimulation: Experimental Studies, Annals of Biomedical Engineering, vol. 34, No. 1, Jan. 2006, pp. 152-160.
R.B. Stein, et al., Encoding Mechanisms for Sensory Neurons Studied with a Multielectrode Array in the Cat Dorsal Root Ganglion, Can. J. Physiol. Pharmacol. 82, (2004), pp. 757-768.
Smit JP, Rutten WL and Boom HB, Endoneural Selective Stimulating Using Wire-Microelectrode Arrays, IEEE Trans Rehabil Eng. Dec. 1999, 7(4), 1 page.
Stephen M. Lawrence, Gurpreet S. Dhillon and Kenneth W. Horch, Fabrication and Characteristics of an Implantable, Polymer-Based, Intrafascicular Electrode, Journal of Neuroscience Methods 131 (2003), pp. 9-26, Elsevier.
Jorge Castro, Pilar Negredo and Carlos Avendano, Fiber Composition of the Rat Sciatic Nerve and its Modification During Regeneration Through a Sieve Electrode, Brain Research, Science Direct, pp. 65-77, Elsevier.
Dustin J. Tyler and Dominique M. Durand, Functionally Selective Peripheral Nerve Stimulation with a Flat Interface Nerve Electrode, IEE Transactions on Neural systems and Rehabilitation Engineering, vol. 10, No. 4 Dec. 2002, pp. 294-303.
Petra Margarete Klinge, et al., Immunohistochemical Characterization of Axonal Sprouting and Reactive Tissue Changes After Long-Term Implantation of a Polyimide Sieve Electrode to the Transected Adult Rat Sciatic Nerve, Biomaterials 22 (2001), pp. 2333-2343, Elsevier.
Kanji Matsukawa, et al., Implantable Microelectrodes with New Electro-Conductive Materials for Recording Sympathetic Neural Discharge, Japanese Journal of Physiology, vol. 53, No. 1, (2003), pp. 61-64.
Daniel McDonnall, et al., Interleaved, Multisite Electrical Stimulation of Cat Sciatic Nerve Produces Fatigue-Resistant Ripple-Free Motor Responses, IEEE Transactions on Neural Systems and Rehabilitation Engineering, vol. 12, No. 2, Jun. 2003, pp. 208-215.
Ken Yoshida, Ksenija Jovanovic and Richard B. Stein, Intrafascicular Electrodes for Stimulation and Recording From Mudpuppy Spinal Roots, Journal of Neuroscience Methods 96 (2000), pp. 47-55, Elsevier.
Natalia Lago, et al., Long Term Assessment of Axonal Regeneration Through Polyimide Regenerative electrodes to Interface the Peripheral Nerve, Biomaterials 26 (2005), Science Direct, pp. 2021-2031, Elsevier.
Robert M. Bradley, et al., Longe Term Chronic Recordings from Peripheral Sensory Fibers Using a Sieve Electrode Array, Journal of Neuroscience Methods 73 (1997), pp. 177-186, Elsevier.
Yuichi Shimatani, Svetlana Grabauskiene and Robert M. Bradley, Long-Term Recording from the Chorda Tympani Nerve in Rats, Physiology & Behavior 76 (2002), pp. 143-149, Elsevier.
Yuichi Shimatani, Stefan A. Nikles, Khalil Najafi and Robert M. Bradley, Long-Term Recordings from Afferent Taste Fibers, Physiology & Behavior 80 (2003), pp. 309-315, Elsevier.
Almut Branner, et al., Long-Term Stimulation and Recording With a Penetrating Microelectrode Array in Cat Sciatic Nerve, IEEE Transactions on Biomedical Engineering, vol. 51, No. 1, Jan. 2004, pp. 146-157.
Li-Jun Li, M.D., Ph.D., et al., Longitudinal Intrafascicular Electrodes in Collection and Analysis of Sensory Signals of the Peripheral Nerve in a Feline Model, Wiley-Liss, Inc. 2005, 5 pages.
Cuoco FA Jr. and Durand DM, Measurement of External Pressures Generated by Nerve Cuff Electrodes, IEEE Trans Rehabil Eng. Mar. 2000; 8(1):35-41., 1 page.
Matthew A. Schiefer, Ronald J. Triolo and Dustin J. Tyler, Models of Selective Stimulation with a Flat Interface Nerve Electrode for Standing Neuroprosthetic Systems, Proceedings of the 28th IEEE, EMBS annual International Conference New York City, USA, Aug. 30-Sep. 3, 2006, pp. 4639-4642.
Charles C. Della Santina, Gregory T.A. Kovacs, and Edwin R. Lewis, Multi-Unit Recording from Regenerated bullfrog Eighth Nerve Using Implantable Silicon-Substrate Microelectrodes, Journal of Neuroscience Methods 72 (1997), pp. 71-86, Elsevier.
Karen A. Moxon, et al., Nanostructured Surface Modification of Ceramic-Based Microelectrodes to Enhance Biocompatibility for a Direct Brain-Machine Interface, IEEE Transactions on Biomedical Engineering, vol. 51, No. 6, Jun. 2004, pp. 881-889.
Dominique M. Durand, Paul Yoo and Zeng Lertmanorat, Neural Interfacing with the Peripheral Nervous System, Proceedings of the 26th Annual International Conference of the IEEE EMBS San Francisco, CA, USA, Sep. 1-5, 2004, pp. 5329-5332.
X. Navarro, Meritxell Vivo and Antoni Valero-Cabre, Neural Plasticity After Peripheral Nerve Injury and Regeneration, Progress in Neurobiology 82 (2007), pp. 163-201, Elsevier.
Fivos Panetos, et al., Neural Prostheses: Electrophysiological and Histological Evaluation of Central Nervous System Alterations Due to Long-Term Implants of Sieve Electrodes to Peripheral Nerves in Cats, IEEE Transactions on Neural systems and Rehabilitation Engineering, vol. 16, No. 3, Jun. 2008, pp. 223-232.
Natalia Lago, et al., Neurobiological Assessment of Regenerative Electrodes for Bidirectional Interfacing Injured Peripheral Nerves, IEEE Transactions on Biomedical Engineering, vol. 54, No. 6, Jun. 2007, pp. 1129-1137.
Stephanie M. Willerth, et al., Optimization of Fibrin Scaffolds for Differentiation of Murine Embryonic Stem Cells into Neural Lineage Cells, Biomaterials 27 (2006), Science Direct, pp. 5990-6003, Elsevier.
Scott F. Lempka, et al., Optimization of Microelectrode Design for Cortical Recording Based on Thermal Noise Considerations, Proceedings of the 28th IEEE EMBS Annual International Conference New York City, USA, Aug. 30-Sep. 3, 2006, pp. 3361-3364.
Stavros Thomopoulos, et al., PDGF-BB Released in Tendon Repair Using a Novel Delivery System Promotes Cell Proliferation and Collagen Remodeling, Journal of Orthopaedic Research, Oct. 2007, pp. 1358-1368, Wiley, InterScience.
Peter Heiduschka, et al., Perforated Microelectrode Arrays Implanted in the Regenerating Adult Central Nervous System, Experimental neurology 171 (2001), pp. 1-10, Academic Press.

(56) References Cited

OTHER PUBLICATIONS

Francisco J. Rodriguez, et al., Polyimide Cuff Electrodes for Peripheral Nerve Stimulation, Journal of Neuroscience Methods 98 (2000), pp. 105-118, Elsevier.

Qing Zhao, et al., Rat Sciatic Nerve Regeneration Through a Micromachined Silicon Chip, Biomaterials 18 (1997), pp. 75-80, Elsevier.

Stephanie M. Willerth, et al., Rationally Designed Peptides for Controlled Release of Nerve Growth Factor from Fibrin Matrices, (2006), pp. 13-23, Wiley InterScience.

Xiujun Zheng, M.D., et al., Recording and Stimulating Properties of Chronically Implanted Longitudinal Intrafascicular Electrodes in Peripheral Fascicles in an Animal Model, 2008, pp. 203-209, Wiley-Liss, Inc.

\* cited by examiner

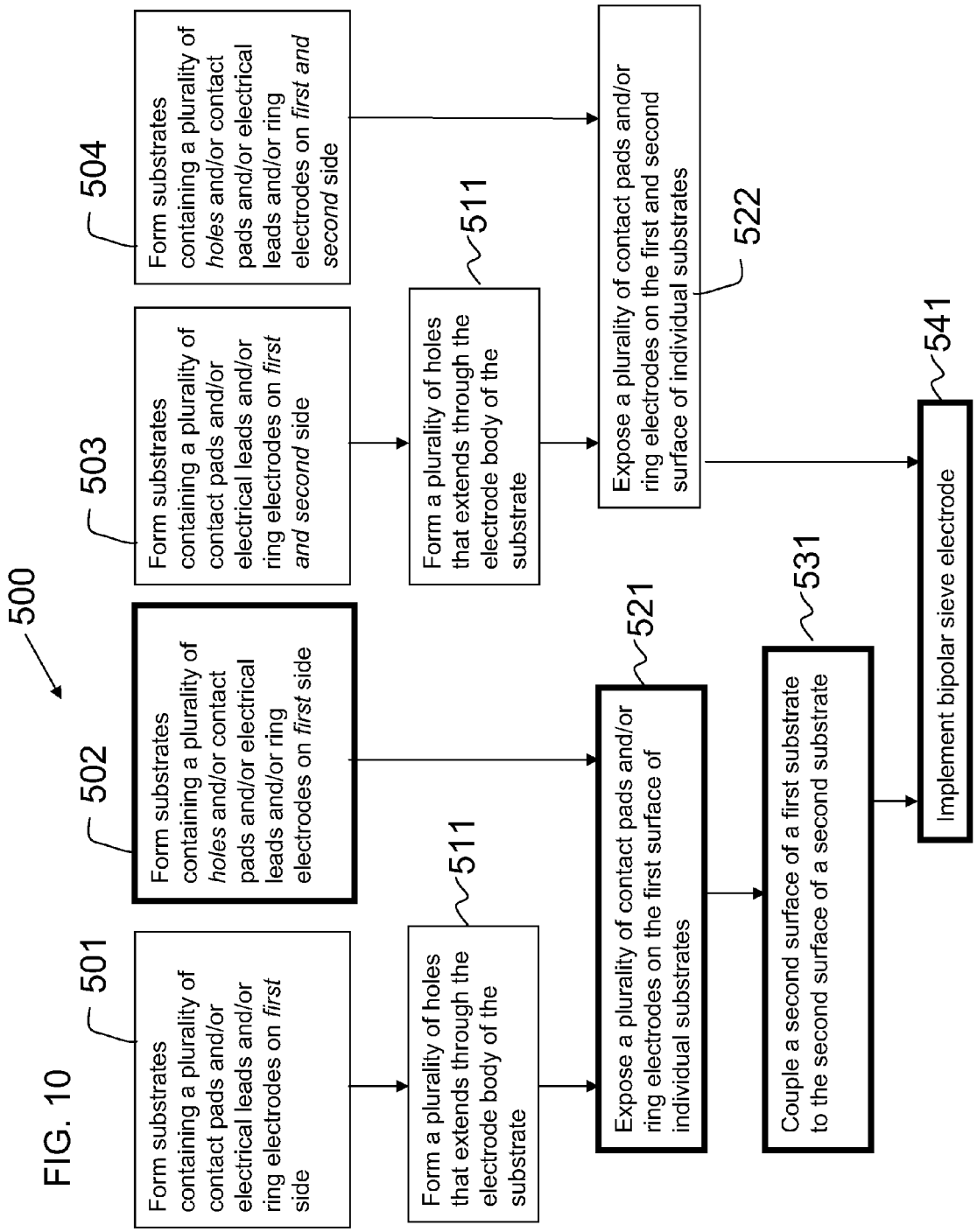

BIPOLAR SIEVE ELECTRODE AND METHOD OF ASSEMBLY

CROSS-REFERENCE TO RELATED APPLICATIONS

This application is a 35 U.S.C. §371 national stage application of PCT/US2009/065462, filed Nov. 23, 2009, which claims priority to U.S. Provisional Application No. 61/116, 995, Nov. 21, 2008, the entireties of which are hereby incorporated by reference for all purposes.

BACKGROUND

A number of existing apparatuses are known for interfacing an external information system with the human nervous system. For example, electrocorticography (ECoG) uses multiple electrode arrays that are placed directly on the surface of a subject's brain to record electrical activity within the cerebral cortex. Because ECoG interfaces cortical tissue, ECoG is a method of interfacing with the central nervous system as a whole. An additional example of an apparatus for use in interfacing the central nervous system is a Utah array. A Utah array is a group of microscopic tines, each containing a number of electrode sites, that are inserted directly into cerebral cortical tissue. An external information system is then electrically coupled to a base portion of the array to facilitate the communication of signals from the information system to the cerebral cortical tissue and/or from the cerebral cortical tissue to the information system. Another example of an apparatus for use in interfacing the central nervous system is a spinal cord stimulation (SCS) system. The SCS system uses small leads, containing multiple electrode sites, placed in close proximity to the spinal cord to communicate, such as delivering and/or receiving, signals between the spinal cord and an external information system.

In addition, a number of apparatuses are available for use in establishing communication between an external information system and a subject's peripheral nervous system. For example, a nerve cuff electrode includes electrical contacts embedded within a conduit that is wrapped around the circumference of a nerve. Connections between the ring electrodes, electrical leads, electrical contacts, and an external information system facilitate communication between the peripheral nerve and an external device. Another example of an apparatus for use in interfacing the peripheral nervous system is a Utah slant array. The Utah slant array is similar to the Utah array discussed above, however, the microscopic tines of the slant array have varying heights that allow the tines to interact with peripheral nervous tissue at different depths of penetration.

Another example of an electrode that may be used to interface the peripheral nervous system is a sieve electrode. A sieve electrode is a thin-film device that contains numerous holes, some of which are surrounded by, or in proximity to, small metal ring electrodes. During use, the electrode is implanted between the two transected ends of a peripheral nerve or trunk, which are microsurgically attached and secured to either side of the device. Axons within the proximal end of the nerve then regenerate through the holes in the electrode, including a number of holes surrounded by, or in proximity to, metal ring electrodes, and functionally reconnect with distal motor and sensory targets. Connections between the metal ring electrodes and an external information system facilitate communication between axons within holes surrounded by metal ring electrodes and an external device. Sieve electrodes are especially useful for the communication of signals from the information system to the peripheral nervous tissue. During this process, pulses of electrical current are delivered to the peripheral nerve tissue via ring electrodes. The delivery of electrical current excites (e.g., depolarizes) local axons resulting in the initiation of action potentials, the basic unit of information within the nervous system. Unfortunately the design of current sieve electrodes is such that electrical stimulation only results in initiation of bidirectional action potentials, or action potentials that simultaneously travel along the target nerve both distally, towards the subject's target muscle or sensory organs, and proximally, towards the subject's spinal cord. Such bi-directional action potentials are particularly undesirable in neuroprosthetic applications due to their lack of directional specificity, and, therefore, functional specificity. For example, electrical stimulation of a nerve for the purpose of activating afferent sensory fibers to induce sensory percepts may result in unwanted, simultaneous motor effects. Similarly, electrical stimulation of a nerve for the purpose of activating efferent motor fibers to induce graded muscle contraction may result in unwanted, simultaneous sensory percepts or the initiation of non-specific muscle reflexes. Accordingly, a sieve electrode that provides directional specificity (i.e., can evoke unidirectional action potentials), and, therefore, functional specificity, is greatly desired.

BRIEF DESCRIPTION

In one aspect, an apparatus is provided for interfacing a nerve and an external information system. The apparatus includes a substrate having a first surface, an opposite second surface, and an electrode body, wherein the electrode body includes a plurality of holes or voids extending therethrough. The apparatus also includes a plurality of electrical leads embedded within the substrate and a plurality of ring electrodes, wherein each of the ring electrodes circumscribes a corresponding hole, and wherein at least a portion of the ring electrodes is positioned on each of the first surface and the second surface.

In another aspect, a neural interface system includes a bipolar sieve electrode applied to a nerve within a subject and an information system positioned external to the subject and configured to transmit signals to the nerve via the bipolar sieve electrode and/or receive signals from the nerve via the bipolar sieve electrode. The bipolar sieve electrode includes one or more substrates having a first surface, an opposite second surface, and an electrode body, wherein the electrode body includes a plurality of holes or voids extending therethrough. The bipolar sieve electrode also includes a plurality of electrical leads embedded within the substrate and a plurality of ring electrodes. Each of the ring electrodes circumscribes, either partially or completely, a corresponding hole, and at least a portion of the ring electrodes is positioned on each of the first surface and the second surface.

In another aspect, a method is provided for assembling a bipolar sieve electrode that interfaces a nerve and an external information system. The method includes forming a plurality of substrates, wherein each substrate includes a plurality of holes or voids extending through the substrate, a plurality of contact pads, a plurality of electrical leads, and/or a plurality of ring electrodes positioned on a first surface and/or a second surface of the substrate. The method also includes exposing the plurality of contact pads and/or the plurality of ring electrodes on the first surface and/or the second surface of each substrate, wherein each of the plurality of ring electrodes circumscribes, either partially or completely, a corresponding hole of the plurality of holes. The method also includes coupling a second surface of a first substrate of the plurality of substrates to a second surface of a second substrate of the plurality of substrates such that at least a portion of the plurality of ring electrodes is positioned on the first surface of each of the first and second substrates.

BRIEF DESCRIPTION OF THE DRAWINGS

The embodiments described herein may be better understood by referring to the following description in conjunction with the accompanying drawings.

FIG. 10 is a flowchart illustrating an exemplary method of assembling a bipolar sieve electrode for providing an interface between a nerve and an external information system.

DETAILED DESCRIPTION

Figure 1:
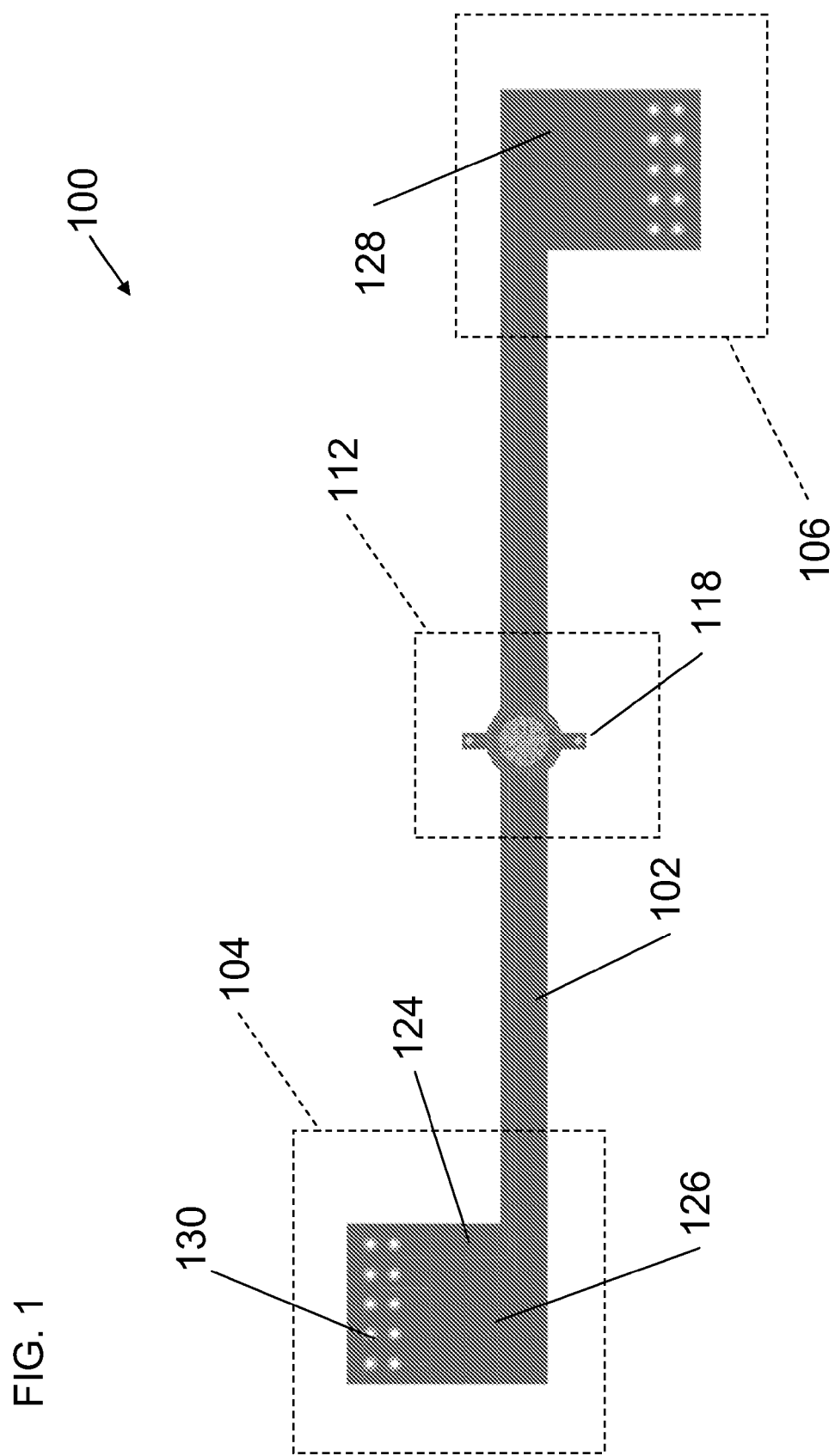
FIG. 1 is a schematic view showing an exemplary bipolar sieve electrode.

The subject matter disclosed herein relates generally to neural interfaces and, more particularly, to an electrode that facilitates achieving communication between the human nervous system and an external system.

While the making and using of various embodiments of the invention are discussed in detail below, it should be appreciated that the embodiments of the invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

While the making and using of various embodiments of the invention are discussed in detail below, it should be appreciated that the embodiments of the invention provides many applicable inventive concepts that may be embodied in a wide variety of specific contexts. The specific embodiments discussed herein are merely illustrative of specific ways to make and use the invention and do not delimit the scope of the invention.

As described below, embodiments of the invention provide a bipolar sieve electrode that provides an interface between a nerve, such as a nerve, nerve root, nerve trunk, nerve division, nerve cord, or nerve branch, within a subject's peripheral nervous system or central nervous system, and an external information system, such as a computer, processor, or controller. The bipolar sieve electrode includes one or more substrates having a first surface, an opposite second surface, and an electrode body, wherein the electrode body includes a plurality of holes or voids extending therethrough. The apparatus also includes a plurality of electrical leads embedded within the substrate and a plurality of ring electrodes, wherein each of the ring electrodes circumscribes, either partially or completely, a corresponding hole, and wherein at least a portion of the plurality of ring electrodes is positioned on each of the first surface and the second surface. Alternatively, the bipolar sieve electrode may include two or more unipolar sieve electrodes that are positioned adjacent each other such that the ring electrodes of each of the unipolar sieve electrodes circumscribe corresponding, aligned holes and face in opposite directions. Alternatively, the bipolar sieve electrode may include two or more joined or linked unipolar sieve electrodes that are folded and coupled such that the ring electrodes of each of the unipolar sieve electrodes circumscribe corresponding, aligned holes and face in opposite directions.

Bipolar sieve electrodes, such as those described in the embodiments included herein, have a unique potential to selectively interface (e.g., stimulate and/or record) small groups of axons within a target nerve. Moreover, bipolar sieve electrodes have a potential to induce unidirectional action potential in local axons within the nerve via bipolar electrical stimulation. In effect, bipolar sieve electrodes are capable of simultaneously recording action potentials, thereby decoding neural signals in multiple sets of sensory and/or motor axons, and initiating action potentials, thereby inducing or modulating neural signals in identical and/or different sets of sensory and/or motor axons. These capabilities enable bipolar sieve electrodes to achieve a real-time interface with peripheral nerve tissue and to access and/or control the neural signals traveling therethrough. Given a general uniformity in peripheral nerve tissue, bipolar sieve electrodes are capable of achieving such a selective interface with any peripheral nerve tissue. Therefore, any procedure and/or event in which neural impulses need to be monitored, recorded, analyzed, controlled, and/or modulated may benefit from the use of a bipolar sieve electrode.

One example of a use for a bipolar sieve electrode is with neuroprosthetic systems. Such systems enable functional electrical stimulation for use in externally controlling muscle activity via motor axon stimulation. External control of muscle activity may be useful in promoting recovery, rehabilitation, and/or remobilization in subjects following injury due to stroke, cerebral palsy, facial nerve palsy or injury, multiple sclerosis, peripheral nerve injury, traumatic brain injury, spinal cord injury, and/or other neurological disabilities. Specifically, such systems may provide significant functional recovery following spinal cord injuries by facilitating control of arm and/or hand function including reaching, grasping, and/or feeding actions, by facilitating control of trunk and/or leg function including standing, transfer, and walking actions, and by facilitating control of autonomic processes including urination, continence, and/or sexual function. Such systems may also provide recovery for such patients by facilitating graded control of muscle contraction for strengthening purposes and/or development of advanced neuroprosthetic systems.

Moreover, such systems also enable functional electrical stimulation for use in externally controlling sensory stimuli via sensory axon stimulation. External control of sensory feedback may be useful in promoting recovery of auditory input including control of afferent neural signals in the cochlear nerve, and/or for use in development of advanced auditory prostheses. Such external control may also be useful in promoting recovery of visual input including control of afferent fibers in the optic nerve, and/or for use in development of advanced visual prostheses. In addition, this external control may be useful in promoting recovery of peripheral sensation including control of afferent neural signals in the peripheral nerve, and/or for use in development of advanced prosthetic limbs for amputees or sensory feedback systems for individuals with other sensory impairments. Such external control may also be useful in promoting modulation and/or treatment of pain disorders by controlling afferent neural signals in a peripheral nerve, leading to development of new approaches to pain management. Additionally, external control may be useful in promoting modulation of afferent vagal nerve activity, cortical activity, and/or visceral, or autonomic sensation. Modulating afferent vagal nerve activity may be useful in promoting the development of advanced treatments for depression and/or development of advanced vagal stimulator systems. Modulating afferent cranial nerve and/or peripheral nerve activity may also effectively modulate cortical activity, which may be useful in influencing and/or studying cortical plasticity and/or re-assignment following neurological injury. Modulating afferent neural signals in gastric nerves and/or in the enteric nervous system may also be useful in modulating appetite, satiety, weight gain, digestion, and/or bowel function. Further, such systems are capable of controlling bioelectric potentials and producing focal electric fields around the ring electrodes in the electrode body, which may enable bioelectric modulation of peripheral nerve regeneration following peripheral nerve injury and/or healing, remodeling, or growth of other types of tissue in proximity to the electrode body. This facilitates development of advanced biomedical systems and methods that are particularly useful within the field of regenerative medicine.

Such systems also enable functional electrical recording of efferent motor signals and/or afferent sensory signals. Recording efferent motor signals may be useful in predicting and/or planning a subject's movements and controlling artificial limbs, robot devices, or graphic interfaces. This facilitates the development of advanced prosthetic limbs and/or neuroprosthetic systems, as well as development of advanced brain-computer interface technology that enables users to directly interface with, for example, vehicles, computers, and/or electronic devices. Recording afferent sensory signals may be useful in re-establishing a sensory connection to the central nervous system, as well as development of advanced visual prostheses and/or development of sensory feedback systems for individuals with central sensory impairments.

Bipolar sieve electrodes, such as those described herein, may also be used in basic science research. For example, bipolar sieve electrodes may be used to acquire single-unit recordings in the peripheral nervous system for studies in sensory and/or motor feedback pathways. Bipolar sieve electrodes may also be used to evoke action potentials in peripheral nervous tissue for studying cortical activity and plasticity in response to altered peripheral input and/or output, and/or studying motor behavior in response to an altered and varied neural input.

Figure 2:
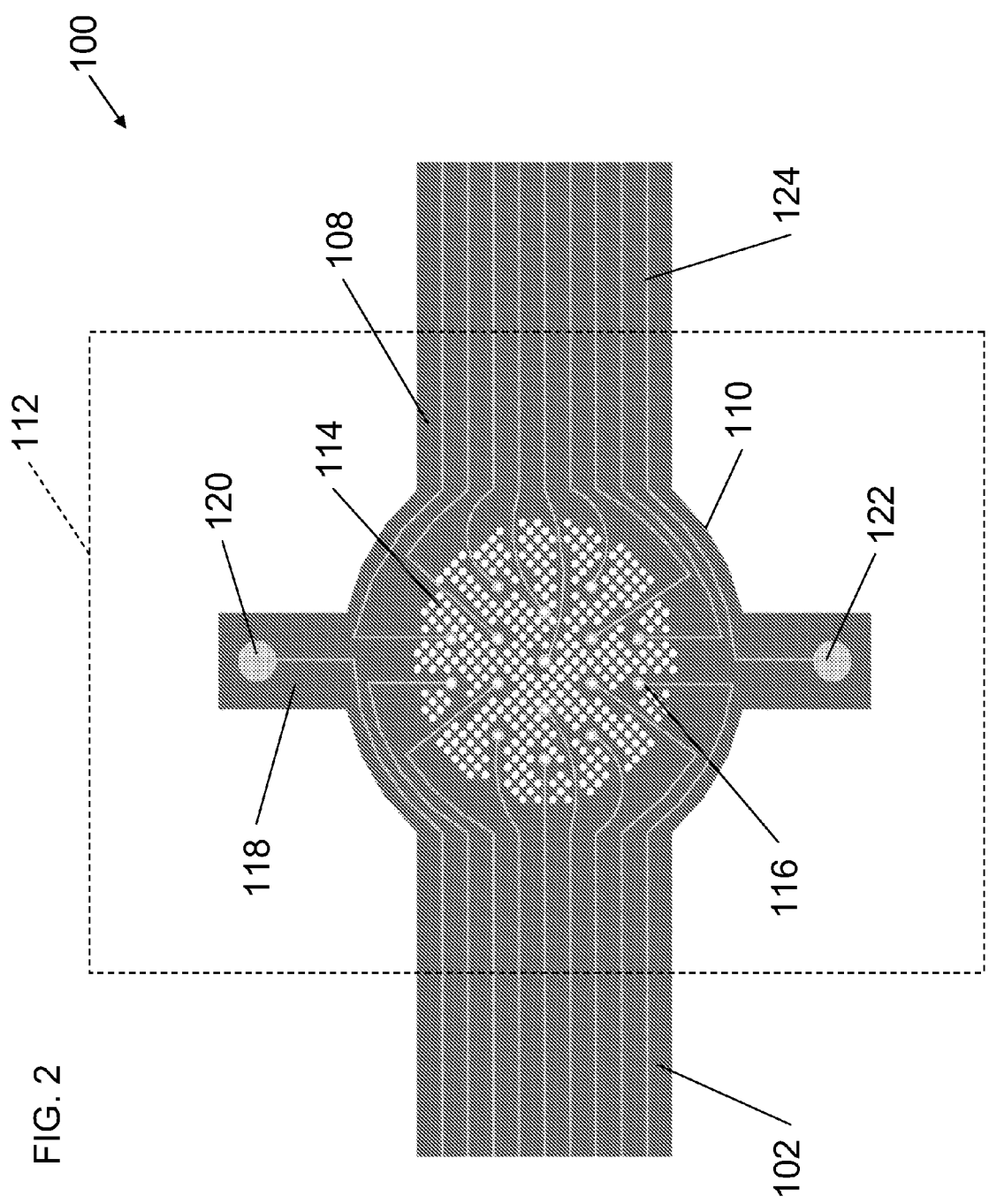
FIG. 2 is a schematic diagram showing an electrode body that may be used with the bipolar sieve electrode shown in FIG. 1.

FIG. 1 is a schematic view showing an exemplary bipolar sieve electrode 100, and FIG. 2 is a schematic diagram showing a central portion that may be used with bipolar sieve electrode 100. Sieve electrode 100 includes a substrate 102 that is composed of, for example, silicon, polyimide, or parylene. In some embodiments, sieve electrode 100 includes two substrates 102 coupled together, or one substrate 102 folded and coupled to itself. In the exemplary embodiment, substrate 102 includes a first end 104 and an opposite second end 106, as well as a first surface 108 and an opposite second surface 110. Substrate 102 also includes an electrode body 112 that includes a plurality of holes or voids 114 extending therethrough. In one embodiment, sieve electrode 100 includes approximately 330 holes extending through electrode body 112. However, it will be understood that sieve electrode 100 may include more or fewer than 330 holes, and that the holes or voids may take a variety of shapes and/or sizes. In the exemplary embodiment, a plurality of ring electrodes 116 are present in or on the substrate 102, wherein each ring electrode 116 completely circumscribes a corresponding hole 114. In one embodiment, sieve electrode 100 includes sixteen ring electrodes 116, wherein at least a portion of the plurality of ring electrodes 116 are present on or applied to each of first surface 108 and second surface 110. However, it will be understood that sieve electrode 100 may include more or fewer than sixteen ring electrodes 116, each of which is electrically isolated, that each ring electrode may either partially or completely circumscribe a corresponding hole, and that each ring electrode may take a variety of shapes and/or sizes. In one embodiment, each ring electrode 116 circumscribes a corresponding hole 114 on first surface 108 and another ring electrode 116 circumscribes the same hole 114 on second surface 110. In another embodiment, each ring electrode 116 circumscribes a corresponding hole 114 on first surface 108 and a different corresponding hole 114 on second surface 110. In the exemplary embodiment, electrode body 112 also includes one or more tabs 118. Each tab 118 may or may not include a reference electrode 120 and/or contact pad 122. Substrate 102 is fabricated and manipulated similar to microchips or integrated circuits in order to form a plurality of electrical leads 124, ring electrodes 116, and connector pads 130 embedded within or applied on substrate 102. More specifically, substrate 102 is subjected to a process such as sacrificial photolithography to expose a portion of the plurality of embedded ring electrodes 116 and connector pads 130.

In one embodiment, a first connecting tab 126 is located at first end 104 and a second connecting tab 128 is located at second end 106, and electrode body 112 is positioned between the first and second connecting tabs 126 and 128. A plurality of contact pads 130 are formed on first surface 108 of substrate 102 and/or second surface 110 of substrate 102. More specifically, contact pads 130 are formed on first connecting tab 126. Moreover, a plurality of contact pads 130 is also formed on first surface 108 of substrate 102 and, more specifically, on second connecting tab 128. Each electrical lead 124 connects a particular contact pad 130 to a corresponding ring electrode 116. Further, reference electrode 120 and contact pad 122 are also connected to a separate contact pad 130 on either first connecting tab 126 or second connecting tab 128 by one electrical lead 124.

In another embodiment, first connecting tab 126 is located at first end 104 and electrode body 112 is located at second end 106. Contact pads 130 are formed on first surface 108 of substrate 102 and, more specifically, on first connecting tab 126. Each electrical lead 124 connects a particular contact pad 130 to a corresponding ring electrode 116. Further, reference electrode 120 and contact pad 122 are also connected to a separate contact pad 130 on first connecting tab 126 by one electrical lead 124.

In another embodiment, sieve electrode 100 does not include either first connecting tab 126 or second connecting tab 128. More specifically, sieve electrode 100 includes only electrode body 112 which includes plurality of holes 114 and plurality of ring electrodes 116 as described above. In the absence of both first connecting tab 126 and second connecting tab 128, contact pads 130 are formed on first surface 108 of substrate 102 and/or second surface 110 of substrate 102 in various geometries around the periphery of electrode body 112. Alternatively, electrical circuitry may be integrated inside substrate 102, or on first surface 108 of substrate 102 and/or second surface 110 of substrate 102, around electrode body 112 in lieu of contact pads 130. In such an embodiment, ring electrodes 116 can be configured to communicate directly (i.e., via secured wire lead or metalized conductors) or indirectly (i.e. via wireless communication paradigms) with an external information system (not shown) via the applied electrical circuitry.

During use, a nerve within a subject, such as a peripheral nerve, nerve root, nerve trunk, nerve division, nerve cord, or nerve branch, is isolated. Bipolar sieve electrode 100, including an encapsulation and/or nerve guidance conduits, is inserted between the transected ends of the isolated nerve. Each end of the transected nerve is then inserted into the nerve guidance conduits (not shown) surrounding the porous area of electrode body 112 and/or secured to sieve electrode 100 such that each end of the nerve is near or in contact with electrode body 112. A drug delivery system, such as a hydrogel or polymeric scaffold, may also be applied within the nerve guidance conduits surrounding the porous area of electrode body 112 and/or applied directly to electrode body 112 of sieve electrode 100. The drug delivery system may facilitate delivery of trophic factors, such as beta-nerve growth factor (β-NGF) or glial-derived neurotrophic factor (GDNF), that enhance peripheral nervous tissue regeneration through plurality of holes 114 in electrode body 112. Each hole 114 has a diameter between approximately 1.0 micrometer (μm) and approximately 1.0 millimeter (mm) (e.g., approximately 60 μm), which enables multiple axons to grow through each hole 114. Delivery of neurotrophic factors around electrode body 112 enhances regeneration of axons through plurality of holes 114 in electrode body 112 and functional reconnection of regenerating axons with distal motor and sensory targets. Moreover, during regeneration, some portion of the plurality of axons extend through holes 114 circumscribed completely by ring electrodes 116. When regeneration is complete, the proximity between axons passing through holes 114 circumscribed by ring electrodes 116 and the ring electrodes 116 themselves facilitates communication of electrical signals between the axons and ring electrodes 116. More specifically, neural signals, such as action potentials, may be initiated in the interfaced axons by sending and electrical stimulus from (1) an external information system (not shown in FIGS. 1 and 2) to (2) one or more contact pads 130, to (3) one or more electrical leads 124 associated with each contact pad 130, to (4) one or more ring electrodes 116 associated with each electrical lead 124, to (5) a specific group of local axons in proximity to the associated ring electrode 116, which become electrically activated. Moreover, neural signals may be recorded from the groups of regenerated axons. More specifically, a neural signal may be transmitted from (1) a number of axons extending through one or more holes 114, to (2) one or more associated ring electrodes 116 circumscribing holes 114, to (3) one or more electrical leads 124 associated with each ring electrode 116, to (4) one or more contact pads 130 associated with each electrical lead 124, to (5) an external information system (not shown in FIGS. 1 and 2).

Figure 3:
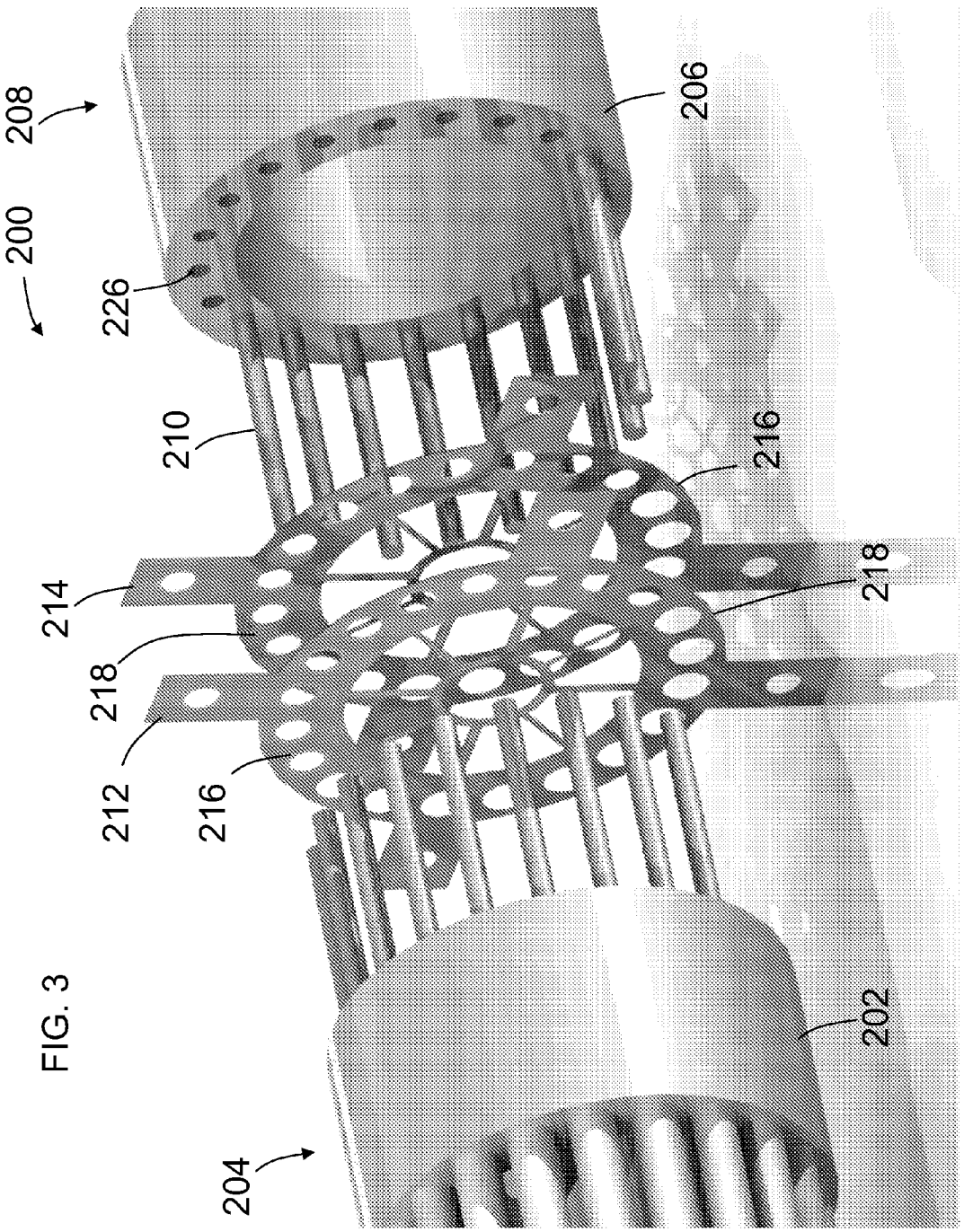
FIG. 3 is a schematic view of an alternative embodiment of a bipolar sieve electrode assembly.
Figure 4:
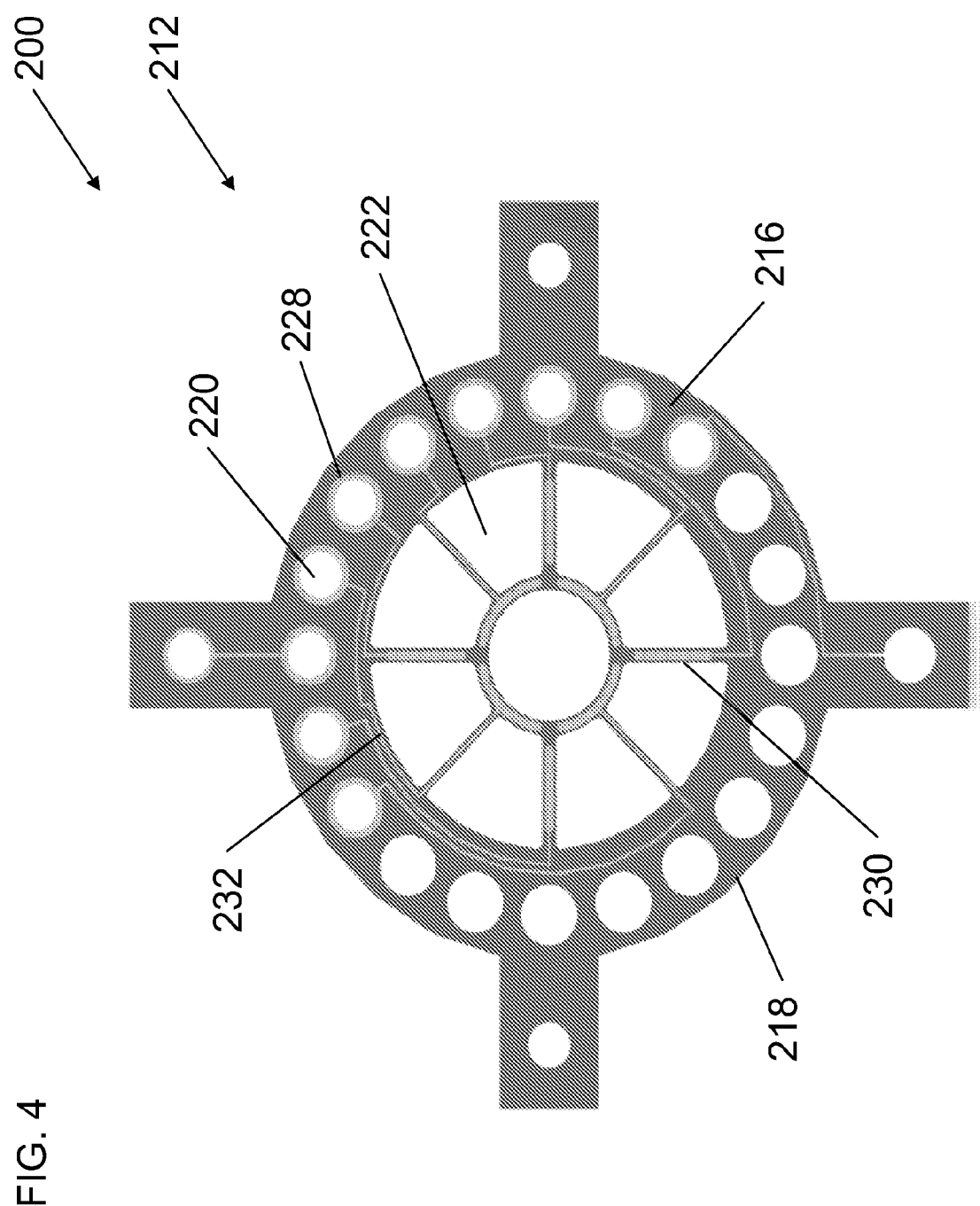
FIG. 4 is a schematic diagram showing an electrode body that may be used with the bipolar sieve electrode assembly shown in FIG. 3.

FIG. 3 is a schematic view of an alternative bipolar sieve electrode assembly 200, and FIG. 4 is a schematic diagram showing an electrode body 212 of an alternative bipolar sieve electrode assembly 200. Sieve electrode assembly 200 includes a first connector assembly 202 located at a first end 204 of sieve electrode assembly 200 and a second connector assembly 206 located at a second end 208 opposite first end 204. Both first and second connector assemblies 202 and 206 include both conductive and non-conductive elements, and may take the form of various types of microelectrode connectors (e.g. printed circuit board, pin connector, insulated microwire array). In the exemplary embodiment, both first and second connector assemblies 202 and 206 include a plurality of male connectors 210 and female connectors that extend therethrough. Sieve electrode assembly 200 also includes a first electrode body 212 and a second electrode body 214, although alternative embodiments may include more than two electrode bodies. Both first electrode body 212 and second electrode body 214 include a first surface 216 and an opposite second surface 218. In one embodiment, first electrode body 212 and second electrode body 214 are coupled by an adhesive element (e.g. chemical adhesive, electrostatic force, mechanical force) that is applied to second surface 218 of each of first and second electrode bodies 212 and 214. In another embodiment, first and second electrode bodies 212 and 214 abut each other but are not coupled by an adhesive element. In some embodiments, spacers or fillers (neither shown) are also be introduced between the first and second electrode bodies 212 and 214 to modulate or control the spatial separation between the two electrode bodies 212 and 214. In the exemplary embodiment, first and second electrode bodies 212 and 214 also include a plurality of contact pads 228 surrounding connector holes 220 that extend through electrode bodies 212 and 214, as well as a plurality of via holes 222 that extend through electrode bodies 212 and 214. Each connector hole 220 is sized to receive an associated male connector 210 therethrough, which makes an electrical connection with connector pad 228, and each via hole 222 is sized to enable passage of a specific amount of regenerating peripheral nervous tissue. Moreover, both connector assemblies 202 and 206 include a plurality of female connectors 226 that are sized to receive an associated male connector 210 therein. For example, a particular male connector 210 extends through first connector assembly 202, first electrode body 212, second electrode body 214, and into a corresponding female connector 226 in second connector assembly 206. At least a portion of the plurality of connector holes 220 in electrode bodies 212 and 214 is circumscribed by an associated contact pad 228. In addition, a plurality of bar electrodes 230 is spaced between each via hole 222. Each bar electrode 230, which partially circumscribes the hole, is connected to an associated contact pad 228 by an electrical lead 232. In some embodiments, ring electrodes 116 (shown in FIG. 1) are embodied by bar electrodes 230.

Figure 5:
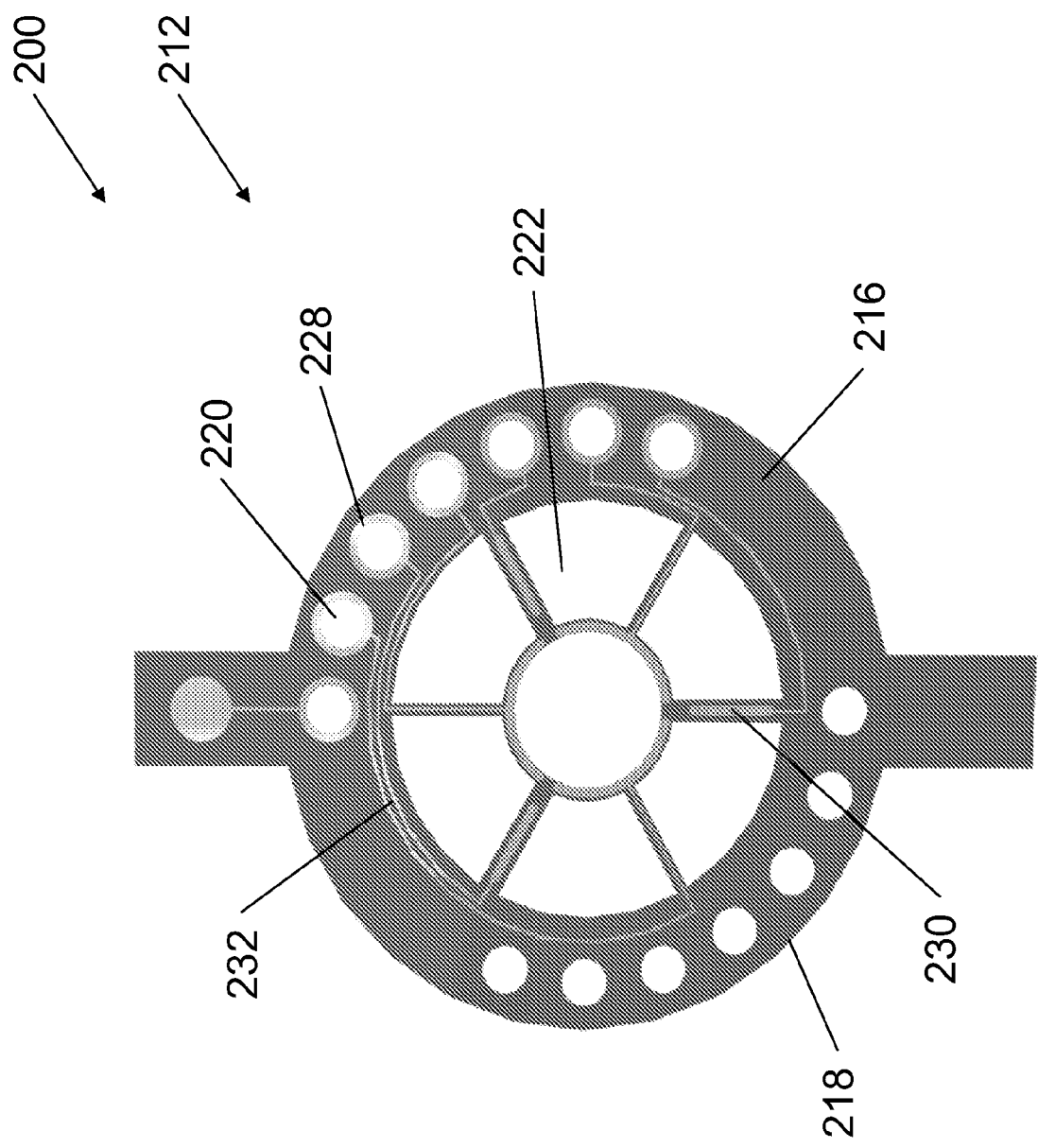
FIG. 5 is an alternative embodiment of the electrode body used with the bipolar sieve electrode assembly shown in FIG. 3.

FIG. 5 is an alternative embodiment of first and second electrode bodies 212 and 214. Each element is identical in FIGS. 3 and 4. As shown in FIG. 4, however, each electrode body 212 and 214 includes nine via holes 222 for peripheral nervous tissue to regenerate through. In contrast, electrode bodies 212 and 214 as shown in FIG. 5 include seven via holes 222 for peripheral nervous tissue to regenerate through. A larger number of smaller via holes 222 facilitates greater control and greater specificity of the neural signals sent and/or received from a nerve using sieve electrode 200. This capability is provided in that each via hole 222 only allows the passage of small numbers of axons or smaller groups of axons, therefore providing electrical communication between individual bar electrodes 230 and smaller populations of axons within the nerve. In contrast, an electrode body 212 or 214 that contains a smaller number of larger via holes 222 would facilitate less control and less specificity of electrical interfacing with peripheral nervous tissue, but may enable enhanced regeneration of peripheral nerve tissue through via holes 222 and enable electrical communication with larger groups of axons. Alternative electrode bodies 212 and/or 214 may simultaneously include via holes or voids 222 and/or bar electrodes 230 of varying sizes, geometries, and/or patterns.

In another alternative embodiment, sieve electrode 200 includes only first electrode body 212. In such an embodiment, at least a portion of the plurality of contact pads 228, electrical leads 232, and bar electrodes 230 are provided on first surface 216 and second surface 218. Moreover, in some embodiments, ring electrodes 116 (shown in FIG. 1) are embodied by bar electrodes 230.

During use, a nerve within a subject, such as a peripheral nerve, nerve root, nerve trunk, nerve division, nerve cord, or nerve branch is isolated. A bipolar sieve electrode, such as sieve electrode 200, including an encapsulation and/or nerve guidance conduits (not shown) is inserted between the transected ends of the isolated nerve. A first end of the transected nerve is then inserted into first connector assembly 202 and secured such that the first end is near or in contact with first electrode body 212, and a second end of the transected nerve is inserted into second connector assembly 206 and secured such that the second end is near or in contact with second electrode body 214. A drug delivery system, such as a hydrogel or polymeric scaffold, may also be applied within one or more connector assemblies 202 and/or 206 surrounding the porous area of electrode bodies 212 and 214 and/or applied directly to electrode bodies 212 and 214 of sieve electrode assembly 200. The drug delivery system may facilitate delivery of trophic factors, such as β nerve growth factors (β-NGF) or glial-derived neurotrophic factor (GDNF), that enhance peripheral nervous tissue regeneration through via holes 222 in electrode bodies 212 and 214. Each via hole 222 is sized to enable multiple groups of axons to grow therethrough. Delivery of neurotrophic factors around electrode bodies 212 and 214 enhances regeneration of axons through via holes 222 in electrode bodies 212 and 214 and functional reconnection of regenerating axons with distal motor and sensory targets. Moreover, during regeneration, some portion of the plurality of axons extends through via holes 222 such that they are in proximity to bar electrodes 230. When regeneration is complete, the proximity between axons passing through via holes 222 and bar electrodes 230 facilitates communication of electrical signals between the axons and bar electrodes 230. More specifically, neural signals, such as action potentials, may be initiated in the interfaced axons by sending an electrical stimulus from (1) an external information system (not shown in FIGS. 3, 4, and 5), to (2) one or more electrically conductive male connectors 210 in connector assemblies 202 and 206, to (3) one or more contact pads 228, to (4) one or more electrical leads 232 associated with each contact pad 228, to (5) one or more bar electrodes 230 associated with each electrical lead 232, to (6) a specific group of local axons in proximity to the associated bar electrodes 230, which becomes electrically activated. Moreover, neural signals may be recorded from the groups of regenerated axons. More specifically, a neural signal may be transmitted from (1) a number of axons extending through one or more via holes 222, to (2) one or more associated bar electrodes 230 in proximity to via holes 222, to (3) one or more electrical leads 232 associated with each bar electrode 230, to (4) one or more contact pads 228 associated with each electrical lead 232, to (5) one or more associated electrically conductive male connectors 210 in connector assemblies 202 and 206, to (6) an external information system (not shown in FIGS. 3, 4, and 5).

Figure 6:
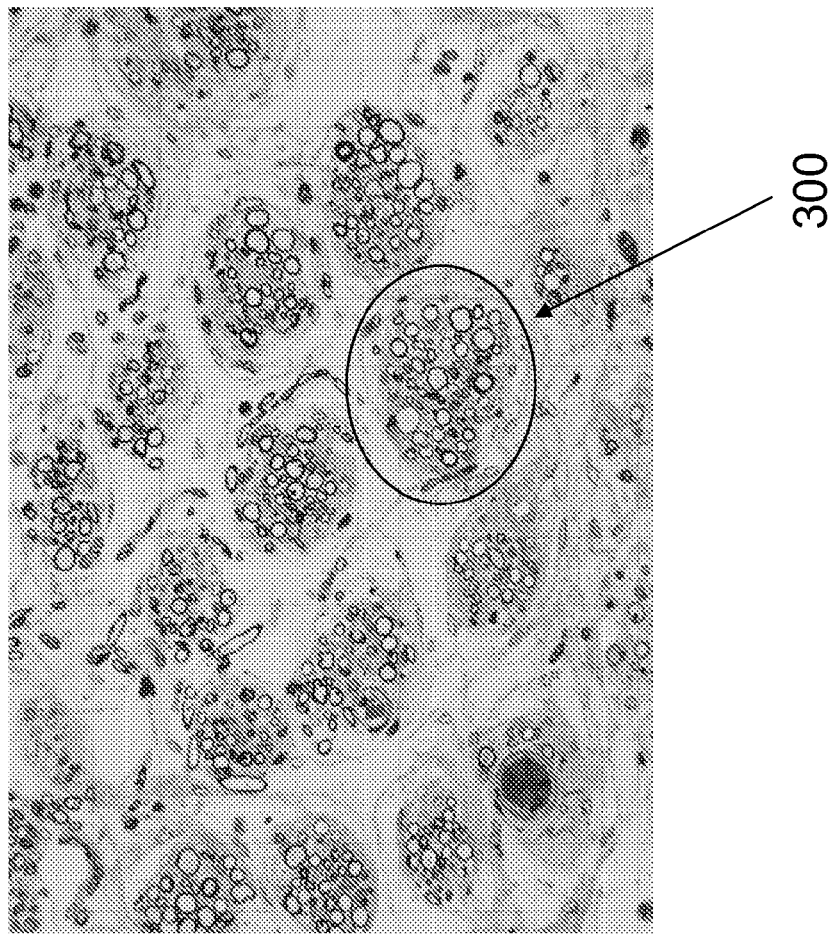
FIG. 6 is an optical micrograph demonstrating small groups of regenerated axons passing through the holes in the electrode body of a sieve electrode.

FIG. 6 is an optical micrograph demonstrating small groups of regenerated axons 300 passing through holes in an electrode body of a sieve electrode, such as those known in the art.

Figure 7:
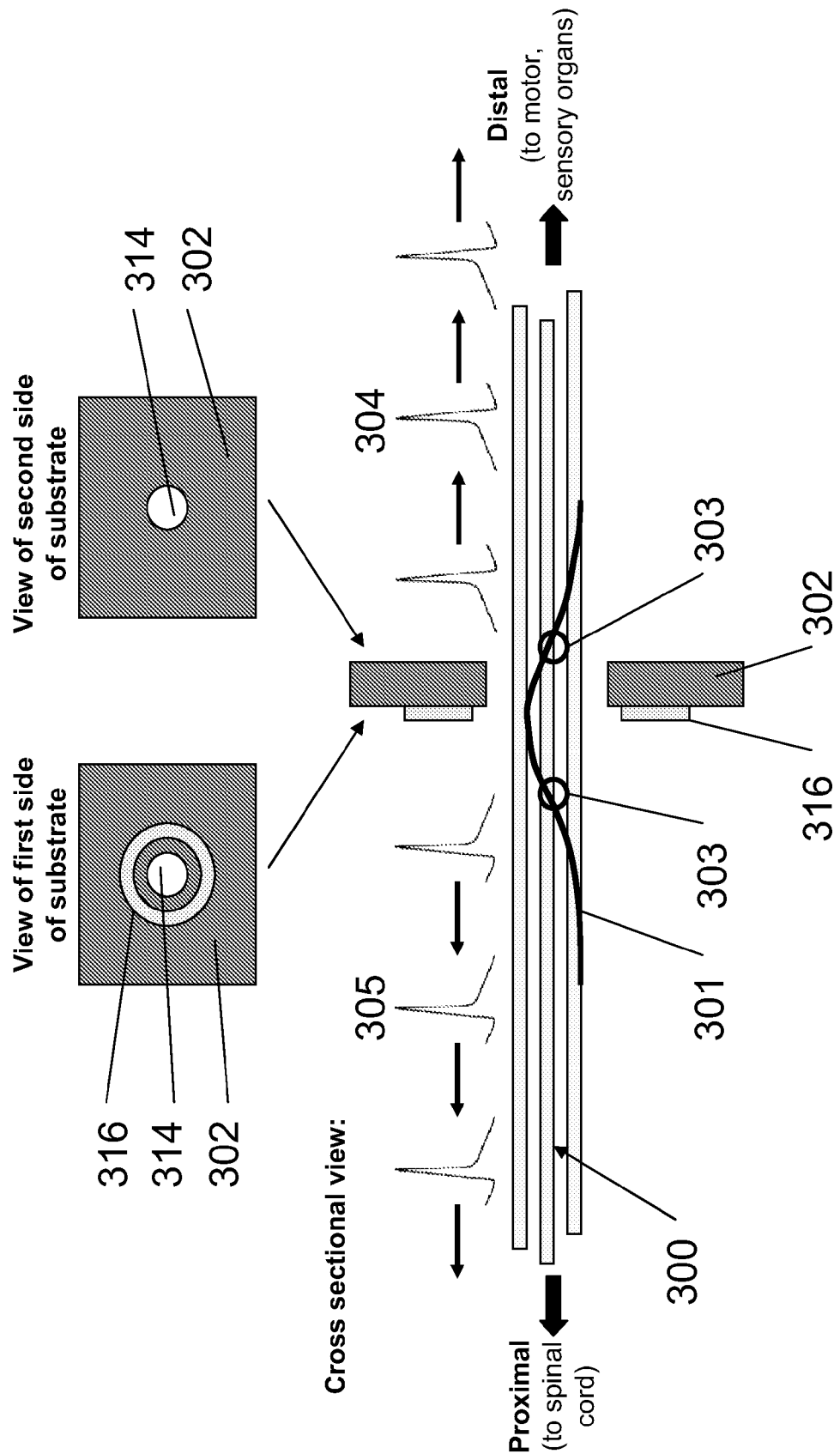
FIG. 7 is a schematic, cross-sectional representation of a number of axons, as shown in FIG. 6, passing through a hole circumscribed by a ring electrode of a unipolar sieve electrode that is known in the art.

FIG. 7 is a schematic, cross-sectional representation of a number of regenerated axons, similar to the small group of axons 300 shown in FIG. 6, passing through a hole 314 in a substrate 302 circumscribed completely by a ring electrode 316 within the electrode body of a unipolar sieve electrode such as those known in the art. As shown in FIG. 7, excitatory pulses of electrical current delivered via ring electrodes 316, as described previously, evoke depolarizing changes in the electrical potential across the membrane of axons 300 extending through the corresponding hole 314. The degree to which the electrical potential across a given patch of axonal membrane changes depends primarily on the distance between ring electrode 316 and the specific patch of axonal membrane. Therefore, the degree of depolarization in the axonal membrane can be represented by a Gaussian curve 301 centered at ring electrode 316, wherein patches of axonal membrane closer to ring electrode 316 are depolarized to a greater degree than those farther away from ring electrode 316. Above a specific threshold (i.e., degree of depolarization) patches of axonal membrane 303 will initiate action potentials 304 and 305, which are propagating waves of depolarization which travel along the length of the axons. Given the pattern of depolarization 301 evoked by stimulation via a unipolar sieve electrode, action potentials are initiated in multiple locations along interfaced axons 303. Due to the lack of inhibitory stimuli, evoked action potentials 304 and 305 propagate in both a distal direction 304 (i.e., toward motor or sensory organs) and in a proximal direction 305 (i.e., towards the spinal cord) along the length of the axons. As mentioned previously, such bi-directional action potentials are particularly undesirable in neuroprosthetic applications due to their lack of directional and functional specificity.

Figure 8:
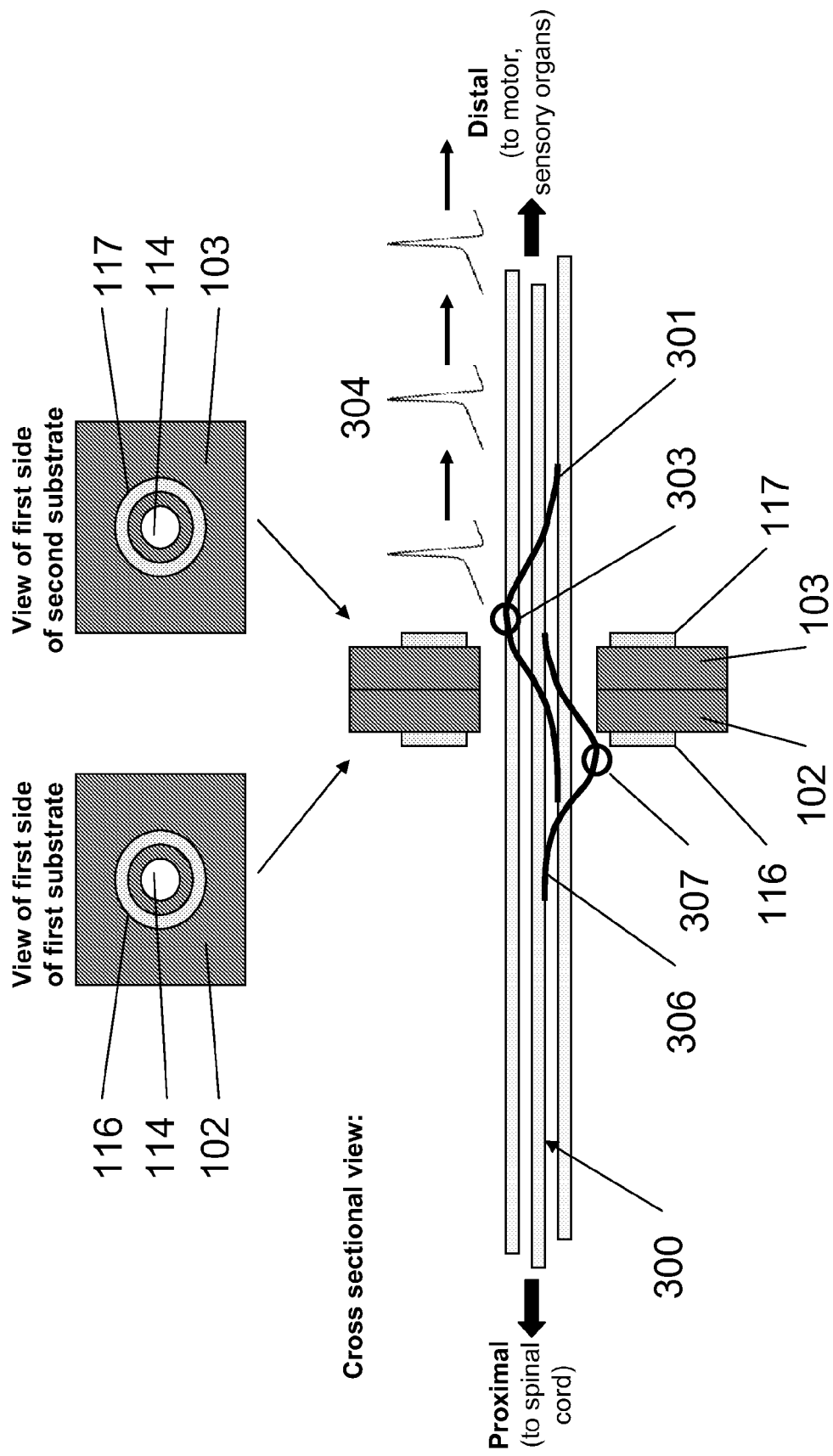
FIG. 8 is a schematic, cross-sectional representation of a number of axons, as shown in FIG. 6, passing through a hole circumscribed by a ring electrode of a bipolar sieve electrode.

FIG. 8 is a schematic, cross-sectional representation of a number of regenerated axons, similar to the small group of axons 300 shown in FIG. 6, passing through an aligned hole 114 in and first substrate 102 and second substrate 103 completely circumscribed by a first ring electrode 116 on the first side of the first substrate 102 and a second ring electrode 117 on the first side of the second substrate 103 within the electrode body 112 of a bipolar sieve electrode 100 (shown in FIGS. 1 and 2). As shown in FIG. 8, excitatory pulses of electrical current delivered via second ring electrode 117, as described previously, evoke depolarizing changes in the electrical potential across the membrane of the axons 300 extending through the corresponding hole 114. Simultaneous application of inhibitory pulses of electrical current delivered via first ring electrode 116, as described previously, evoke hyperpolarizing changes in the electrical potential across the membrane of the axons 300 extending through the corresponding hole 114. The degree to which the electrical potential across a given patch of axonal membrane changes due to both of these stimuli depends on: 1) the distance between first ring electrode 116 and the specific patch of axonal membrane, 2)

the distance between second ring electrode 117 and the specific patch of axonal membrane, 3) the linear distance between first ring electrode 116 and second ring electrode 117, and 4) the temporal separation between the electrical activation of the first ring electrode 116 and the second ring electrode 117. Therefore, the degree of depolarization in the axonal membrane can be represented by two superimposed Gaussian curves 301 and 306 centered at second ring electrode 117 and first ring electrode 116, respectively. Patches of axonal membrane closer to second ring electrode 117 will be depolarized to a greater degree than those farther away from second ring electrode 117, and patches of axonal membrane closer to first ring electrode 116 will be hyperpolarized to a greater degree than those farther away from first ring electrode 116. Above a specific threshold (i.e., degree of depolarization) patches of axonal membrane 303 will initiate action potentials. Yet, simultaneously, below a specific threshold (i.e., degree of hyperpolarization) patches of axonal membrane 307 will become resistant to action potential conduction and will effectively block action potential propagation. Given this pattern of depolarization 301 and hyperpolarization 306 evoked by bipolar stimulation via a bipolar sieve electrode, action potentials are initiated in multiple locations along interfaced axons 303 yet the evoked action potentials 304 only successfully propagate in the distal direction 304 (i.e., toward motor or sensory organs) as action potentials propagating in the proximal direction are effectively blocked by a region of unresponsive, hyperpolarized axonal membrane 307. Alternatively, electrical stimulation via bipolar sieve electrodes could also be utilized to selectively initiate action potentials propagating solely in the proximal direction (i.e., toward the spinal cord). Such unidirectional action potentials could be initiated simply by switching the polarity of the electrical stimulus delivered to the two ring electrodes, effectively delivering excitatory pulses of electrical current through first ring electrode 116 and inhibitory pulses of electrical current through second ring electrode 117. Varying the spatial and temporal separation of the electrical activation of first ring electrode 116 and second ring electrode 117 could also be utilized to control the selective initiation of unidirectional action potentials as various stimulus waveforms and temporal delays between stimuli activate different populations of axons within interfaced nervous tissue. Selective initiation of unidirectional action potential in specific groups of interface axons 300 may also be achieved through the use of more than two substrates 102 and more than two electrodes 116 and 117 positioned along the length of regenerated axons, thereby enabling complex multi-polar stimulation of interfaced axons 300. As mentioned previously, such selective initiation of unidirectional action potentials (in either the proximal or distal direction) is particularly useful and sought after in the field.

Figure 9:
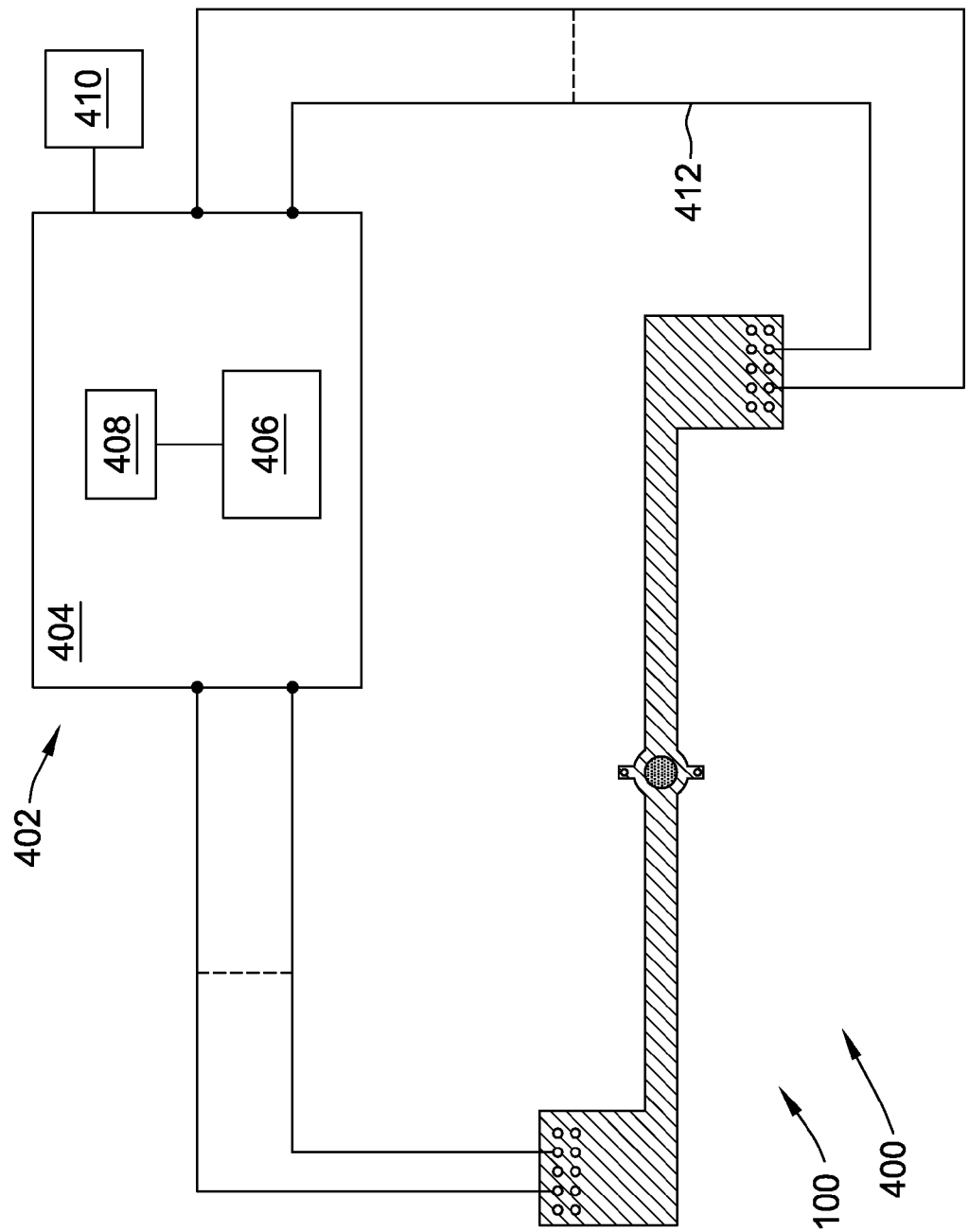
FIG. 9 is a block diagram showing an exemplary neural interface system that includes a bipolar sieve electrode.

FIG. 9 is a block diagram showing an exemplary neural interface system 400. System 400 includes an information system 402 that is positioned external to a subject, and a bipolar sieve electrode 100 or 200. Alternatively, information system 402 may be positioned internal to the subject. Information system 402 includes, for example, a computing device, controller, or computer 404. Computer 404 includes a processor 406 and a system memory 408 coupled to processor 406. Computer 406 also includes an input device 410, such as a mouse and/or a keyboard. A lead wire 412 is connected to one of a plurality of outputs 414 of information system 402 and to a corresponding contact pad 130 (shown in FIGS. 1 and 2) to facilitate transmitting signals between information system 402 and sieve electrode 100 or 200, as described previously. In an alternative embodiment electrical impulses or digital signals are communicated wirelessly (i.e. without lead wire 412) from information system 402, positioned either internal or external to the subject, to a corresponding contact pad 130 on the electrode (shown in FIGS. 1 and 2). In such an embodiment, wireless communication between information system 402 and bipolar sieve electrode 100 or 200 may take the form of radio frequency (RF) communication, transcutaneous current routing, optical communication, and/or any other suitable wireless communication method.

Computer 404 as described herein may have more than one processor 406 as well as storage memory separate from system memory 408. Computer 404 typically includes at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

In some embodiments, processor 406 includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor. Moreover, in some embodiments, information system 402 may include a database (not shown) that stores any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Further, aspects of the invention are operable with any memory area and means for storing or retrieving data.

FIG. 10 is a flowchart 500 illustrating an exemplary method, and alternative methods, of assembling a bipolar sieve electrode, such as bipolar sieve electrode 100 (shown in FIGS. 1 and 2) or bipolar sieve electrode 300 (shown in FIGS. 3-5), for providing an interface between a nerve and an external information system, such as information system 402 (shown in FIG. 9). In the exemplary embodiment, two identical substrates 102 are formed using known techniques 502. Each substrate 102 includes a first surface 108 and a second surface 110 and contains a plurality of holes 114, contact pads 130, electrical leads 124, and/or ring electrodes 116 on or in first surface 108 (each shown in FIGS. 1 and 2). Second, a plurality of contact pads 130 and/or ring electrodes 116 are exposed 521 on first surface 108 of each substrate 102. More specifically, each ring electrode 116 circumscribes a corresponding hole 114 within electrode body 112 of substrate 102. In the exemplary embodiment, contact pads 130 and/or ring electrodes 116 are exposed at a first end 104 (shown in FIGS. 1 and 2) and additional contact pads 130 and/or ring electrodes 116 are exposed at a second end 106 (shown in FIGS. 1 and 2), such that electrode body 112 of each substrate 102 is located between first end 104 and second end 106. In other embodiments, contact pads 130 and/or ring electrodes 116 are exposed only at a first end 104, such that electrode body 112 forms second end 106 of substrate 102. A plurality of ring electrodes 116 may also be applied or formed in or on first surface 108 of substrate 102. Thereafter, second surface 110 of one substrate 102 is coupled 531 together with second surface 110 of another substrate 102 such that at least a portion of the plurality of ring electrodes 116 is positioned on first surface 108 of each substrate 102 and such that at least a portion of the plurality of ring electrodes 116 on first and second substrate 102 circumscribe corresponding, aligned holes 114.

In an alternative method, two identical substrates 102 are formed using known techniques 501. Each substrate 102 includes a first surface 108 and a second surface 110 and contains a plurality of contact pads 130, electrical leads 124, and/or ring electrodes 116 on or in first surface 108 of substrate 102, but does not initially contain any holes 114. In such an embodiment, an additional step must be taken to form a plurality of holes 511 that extend through the electrode body 112 of the substrate 102 prior to exposure of a plurality of electrical elements 521, and coupling of multiple substrates 531, as described in the exemplary method.

In another alternative embodiment, bipolar sieve electrode 100 or 200 includes only a single substrate 102, rather than two coupled substrates. In a method for assembling such a bipolar sieve electrode, substrate 102 is formed 504. Substrate 102 includes a first surface 108 and a second surface 110 and contains a plurality of holes 114, contact pads 130, electrical leads 124, and/or ring electrodes 116 on or in both first surface 108 and second surface 110 of substrate 102. Second, a plurality of contact pads 130 and/or ring electrodes 116 are exposed 522 on both first surface 108 and second surface 110 of substrate 102. More specifically, each ring electrode 116 is exposed such that it circumscribes a corresponding hole 114 within electrode body 112 of substrate 102, such that at least a portion of the plurality of ring electrodes 116 is positioned on both first surface 108 and second surface 110 of substrate 102, and such that at least a portion of the plurality of ring electrodes 116 on first surface 108 and second surface 110 of substrate 102 circumscribe corresponding holes 114. This method of fabricating a bipolar sieve electrode 100 or 200 containing only a single substrate 102 may also be applied where substrate 102 is formed 504 and then folded, manipulated, and/or arranged in three-dimensional space prior to exposure of any plurality of contact pads 130 and/or ring electrodes 116 on either first surface 108 and/or second surface 110 of substrate 102.

In an alternative method for the fabrication of a bipolar sieve electrode 100 or 200 containing only a single substrate 102, substrate 102 is formed 503. Substrate 102 includes a first surface 108 and a second surface 110 and contains a plurality of contact pads 130, electrical leads 124, and/or ring electrodes 116 on or in both first surface 108 and second surface 110 of substrate 102, but does not initially contain any holes 114. In such an embodiment, an additional step must be taken to form a plurality of holes 511 that extend through electrode body 112 of substrate 102 prior to exposure of a plurality of electrical elements 522 on both first surface 108 and second surface 110 of substrate 102. This method of fabricating a bipolar sieve electrode 100 or 200 containing only a single substrate 102 may also be applied where substrate 102 is formed 504 and then folded, manipulated, and/or arranged in three-dimensional space prior to formation of a plurality of holes 511 that extend through electrode body 112 of substrate 102 and prior to exposure of a plurality of electrical elements 522 on either first surface 108 and/or second surface 110 of substrate 102.

It will be understood that the particular embodiments described herein are shown by way of illustration and not as limitations of the invention. The principal features of this invention may be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein may be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An apparatus for providing an interface between a nerve and an external information system, said apparatus comprising:
    a substrate comprising a first surface, an opposite second surface, and an electrode body, said electrode body comprises a plurality of holes extending therethrough;
    a plurality of electrical leads embedded on or in said substrate; and
    a plurality of ring electrodes, each of said plurality of ring electrodes circumscribing, either partially or completely, a corresponding one of said plurality of holes, wherein at least a portion of said plurality of ring electrodes is positioned on each of said first surface and said second surface such that, for each corresponding hole, a first ring electrode on said first surface circumscribes a first end of the hole and a second ring electrode on said second surface circumscribes an opposite second end of the hole such that said substrate is positioned between said first and second ring electrodes.

2. An apparatus in accordance with claim 1, wherein said substrate further comprises a first end and an opposite second end.

3. An apparatus in accordance with claim 2, wherein each of said first end and said second end comprises a plurality of electrical contacts, each of said plurality of electrical contacts is coupled to a corresponding electrical lead of said plurality of electrical leads.

4. An apparatus in accordance with claim 2, wherein said first end comprises a plurality of electrical contacts, each of said plurality of electrical contacts is coupled to a corresponding electrical lead of said plurality of electrical leads, and wherein said second end comprises said electrode body.

5. An apparatus in accordance with claim 1, wherein said electrode body comprises at least one tab comprising one of at least one reference electrode and at least one contact pad.

6. An apparatus in accordance with claim 1, wherein said substrate comprises a first substrate and a second substrate coupled together such that a first surface of said first substrate is oriented in a first direction and a first surface of said second substrate is oriented in a second direction opposite the first direction, with a second surface of said first substrate coupled to a second surface of said second substrate.

7. An apparatus in accordance with claim 1, wherein each of said plurality of ring electrodes is electrically isolated from all other ring electrodes of said plurality of ring electrodes.

8. An apparatus in accordance with claim 1, wherein each of said ring electrodes is configured to communicate wirelessly with the external information system.

9. An apparatus in accordance with claim 1, wherein an interface between said plurality of ring electrodes and the nerve is enhanced by controlled delivery of trophic factors or molecular compounds.

10. A neural interface system comprising:
a bipolar sieve electrode adapted to be applied to a nerve within a subject, said bipolar sieve electrode comprising:
a substrate comprising a first surface, an opposite second surface, and an electrode body, said electrode body comprises a plurality of holes extending therethrough;
a plurality of electrical leads embedded within said substrate; and
a plurality of ring electrodes, each of said plurality of ring electrodes circumscribing, either partially or completely, a corresponding one of said plurality of holes, wherein at least a portion of said plurality of ring electrodes is positioned on each of said first surface and said second surface such that, for each corresponding hole, a first ring electrode on said first surface circumscribes a first end of the hole and a second ring electrode on said second surface circumscribes an opposite second end of the hole such that said substrate is positioned between said first and second ring electrodes; and
an information system positioned external to the subject and configured to transmit signals to the nerve via said bipolar sieve electrode and receive signals from the nerve via said bipolar sieve electrode.

11. A neural interface system in accordance with claim 10, wherein said substrate further comprises a first end and an opposite second end.

12. A neural interface system in accordance with claim 11, wherein each of said first end and said second end comprises a plurality of electrical contacts, each of said plurality of electrical contacts is coupled to a corresponding electrical lead of said plurality of electrical leads.

13. A neural interface system in accordance with claim 11, wherein said first end comprises a plurality of electrical contacts, each of said plurality of electrical contacts is coupled to a corresponding electrical lead of said plurality of electrical leads, and wherein said second end comprises said electrode body.

14. A neural interface system in accordance with claim 10, wherein said substrate comprises a first substrate and a second substrate coupled together such that a first surface of said first substrate is oriented in a first direction and a first surface of said second substrate is oriented in a second direction opposite the first direction, with a second surface of said first substrate coupled to a second surface of said second substrate.

15. A neural interface system in accordance with claim 10, wherein each of said plurality of ring electrodes is electrically isolated from all other ring electrodes of said plurality of ring electrodes.

16. A neural interface system in accordance with claim 10, wherein each of said ring electrodes is configured to communicate wirelessly with the external information system.

* * * * *